(12) United States Patent
Sisk et al.

(10) Patent No.: US 8,062,771 B2
(45) Date of Patent: *Nov. 22, 2011

(54) AMBIPOLAR HOST IN ORGANIC LIGHT EMITTING DIODE

(75) Inventors: David T. Sisk, San Diego, CA (US); Sheng Li, Vista, CA (US); Amane Mochizuki, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 4 days.

This patent is subject to a terminal disclaimer.

(21) Appl. No.: 12/694,939

(22) Filed: Jan. 27, 2010

(65) Prior Publication Data

US 2010/0213452 A1 Aug. 26, 2010

Related U.S. Application Data

(60) Provisional application No. 61/149,560, filed on Feb. 3, 2009.

(51) Int. Cl.
*H01L 51/54* (2006.01)
*C07D 401/14* (2006.01)

(52) U.S. Cl. ........ 428/690; 428/917; 313/504; 313/506; 546/256

(58) Field of Classification Search .................. None
See application file for complete search history.

(56) References Cited

U.S. PATENT DOCUMENTS

| | | | |
|---|---|---|---|
| 2002/0024293 A1 | 2/2002 | Igarashi et al. | |
| 2002/0034656 A1 | 3/2002 | Thompson et al. | |
| 2003/0072964 A1* | 4/2003 | Kwong et al. | 428/690 |
| 2003/0124381 A1* | 7/2003 | Thompson et al. | 428/690 |
| 2004/0024293 A1 | 2/2004 | Lawrence | |
| 2005/0127823 A1 | 6/2005 | Iwakuma et al. | |
| 2005/0282036 A1* | 12/2005 | D'Andrade et al. | 428/690 |
| 2006/0222886 A1 | 10/2006 | Kwong et al. | |
| 2007/0015006 A1 | 1/2007 | Lee et al. | |
| 2007/0075631 A1 | 4/2007 | Tung et al. | |
| 2008/0166591 A1 | 7/2008 | Yamada | |

FOREIGN PATENT DOCUMENTS

| | | |
|---|---|---|
| EP | 1857521 * | 11/2007 |
| EP | 1857521 A1 | 11/2007 |
| EP | 1858094 | 11/2007 |
| JP | 2004-273190 | 9/2004 |
| JP | 2007-291092 A | 11/2007 |
| JP | 2008-115131 * | 5/2008 |
| JP | 2008-120696 A | 5/2008 |
| WO | WO03078541 A1 | 9/2003 |
| WO | WO2004074399 A1 | 9/2004 |
| WO | WO2006080229 A1 | 8/2006 |
| WO | WO2008027132 A1 | 3/2008 |
| WO | WO 2010/090925 A1 | 8/2010 |

OTHER PUBLICATIONS

Machine-generated translation for JP 2004-273190, which was published Sep. 2004.*

D'Andrade, et al., White Organic Light-Emitting Devices for Solid-State Lighting, *Adv. Mater.* 16, 1585, 2004.
D'Andrade, et al., White Light Emission Using Triplet Excimers in Electrophosphorescent Organic Light-Emitting Devices, *Adv. Mater.* 14, 1032, 2002.
D'Andrade, et al., Efficient Organic Electrophosphorescent White-Light-Emitting Device with a Triple Doped Emissive Layer, *Adv. Mater.* 16, 624, 2004.
Adachi, et al., Nearly 100% Internal Phosphorescence Efficiency in an Organic Light Emitting Device, *J. Appl. Phys.* 90, 5048, 2001.
Wu, et al., Highly Efficient White-Electrophosphorescent Devices Based on Polyfluorene Copolymers Containing Charge-Transporting Pendent Units, *J. Mater. Chem.* 17, 167, 2007.
Cheng, et al., White Organic Light-Emitting Devices Using a Phosphorescent Sensitizer, *Appl. Phys. Lett.* 82, 4224, 2003.
Seo, et al., Highly Efficient White Organic Light-Emitting Diodes using Two Emitting Materials for Three Primary Colors (red, green, and blue), *Appl. Phys. Lett.* 90, 203507, 2007.
Kido, et al., Pyridine-Containing Bipolar Host Materials for Hightly Efficient Blue Phosphorescent OLED's, *Chem. Mater.* 2008, 20(5), 1691-1693.
Baldo, et al., High-Efficiency Fluorescent Organic Light-Emitting Devices Using a Phosphorescent Sensitizer, *Nature*, 403, 750, 2000.
Guan, et al., The Host Materials Containing Carbazole and Oxadiazole Fragment for Red Triplet Emitter in Organic Light-Emitting Diodes, *Org. Electronics*, 7, 330-336, 2006.
Chen, et al., White Organic Light-Emitting Devices with a Bipolar Transport Layer Between Blue Fluorescent and Orange Phosphorescent Emitting Layers, *Appl. Phys. Lett.* 91, 023505, 2007.

(Continued)

*Primary Examiner* — Dawn L. Garrett
(74) *Attorney, Agent, or Firm* — Knobbe Martens Olson & Bear LLP

(57) ABSTRACT

Some embodiments provide a compound represented by Formula 1:

(Formula 1)

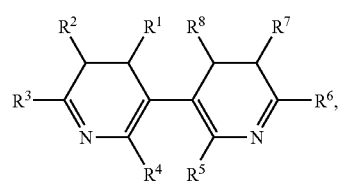

wherein $R^1$, $R^2$, $R^3$, $R^6$, $R^7$, and $R^8$ are independently selected from the group consisting of H, optionally substituted $C_{1-12}$ alkyl, optionally substituted phenyl, optionally substituted carbazolyl, optionally substituted diphenylamine and optionally substituted diphenylaminophenyl; provided that: at least one of $R^1$, $R^2$, and $R^3$ is selected from optionally substituted carbazolyl, optionally substituted diphenylamine and optionally substituted diphenylaminophenyl and at least one of $R^6$, $R^7$, and $R^8$ is selected from optionally substituted carbazolyl, optionally substituted diphenylamine and optionally substituted diphenylaminophenyl; and $R^4$ and $R^5$ are independently selected from the group consisting of H, optionally substituted $C_{1-12}$ alkyl, optionally substituted phenyl, optionally substituted diphenylamine and optionally substituted diphenylaminophenyl. Other embodiments provide an organic light-emitting diode device comprising a compound of Formula I.

20 Claims, 3 Drawing Sheets

OTHER PUBLICATIONS

Cai, et al., Electron and Hole Transport in a Wide Bandgap Organic Phosphine Oxide for Blue Electrophosphorescence, *Appl. Phys. Lett.* 92, 083308, 2008.

Sun, et al., Management of Singlet and Triplet Excitons for Efficient White Organic Light-Emitting Devices, *Nature*, 440, 908, 2006.

Machine translation for JP2004-273190, Sep. 2004 in 44 pages.

Su Shi-Jian, et al., "Pyridine-Containing Bipolar Host Materials for Highly Efficient Blue Phosphorescent OLEDs" Chemistry of Materials, American Chemical Society, Washington, US, vol. 20, Jan. 1, 2008, pp. 1691-1693, XP002535894, ISSN: 0897-4756.

Office Action in U.S. Appl. No. 12/694,984, dated Mar. 17, 2011.
Office Action in U.S. Appl. No. 12/694,920, dated Feb. 18, 2011.
Office Action in U.S. Appl. No. 12/694,981, dated Mar. 18, 2011.
Office Action in U.S. Appl. No. 12/695,000, dated Mar. 25, 2011.
Office Action in U.S. Appl. No. 12/694,994, dated Mar. 17, 2011.

\* cited by examiner

AMBIPOLAR HOST IN ORGANIC LIGHT EMITTING DIODE

CROSS-REFERENCE TO RELATED APPLICATIONS

This application claims the benefit of U.S. Provisional Application No. 61/149,560, filed Feb. 3, 2009, which is incorporated by reference herein in its entirety.

BACKGROUND OF THE INVENTION

1. Field of the Invention

This invention relates to compounds for use in organic light emitting diodes, such as for host materials.

2. Description of the Related Art

White organic light emitting devices (WOLEDs) have attracted much attention and been intensively studied due to their potential applications as backlight sources, full color displays, and general lighting. Among various device configurations to produce white light, a single-emissive-layer device employing phosphorescent materials in combination with proper host materials is desirable. Some advantages of such device may include reduced overall cost, increased quantum efficiency and easier fabrication. Since phosphorescent emitters can harvest both singlet and triplet excitons, it may lead to the potential of achieving 100% internal quantum efficiency. Adding host materials may also reduce concentration quenching of the emissive materials and further increase the efficiency. In addition, adding host materials reduces the required amount of expensive emissive material, and the fabrication of a single layer device is easier and more cost effective than a multiple layer device. As a result, the single-emissive-layer device with phosphorescent and host materials can lower the overall cost of fabricating the WOLEDs.

The use of effective host materials is important in making efficient WOLEDs. A host may be improved if it transports both holes and electrons efficiently at the same speed. A host may also be improved if its triplet energy is high enough to effectively confine the triplet excitons on the guest molecules. Most currently used host materials are a mixture of hole-transport material and electron-transport material, which may pose potential problems of phase separation, aggregation and lack of uniformity, and unequal material degradation rates. Thus, development of an ambipolar single molecule (i.e., a molecule capable of transporting both holes and electrons effectively) for a host material would be useful.

Some ambipolar single molecule hosts have been used in either single colour or white OLED device applications. However, these molecules have either unbalanced hole-transport and electron-transport properties, or the devices made from these molecules have only moderate efficiency.

Thus there is a need for a new type of ambipolar host that can be easily synthesized, possesses high thermal and electrochemical stability, and has well balanced hole-transport and electron-transport mobility when used as a host for phosphorescent emissive materials. Such a host may be used to achieve a simple device structure with high quantum efficiency and low turn-on voltage.

SUMMARY OF THE INVENTION

Some embodiments provide a compound represented by Formula 1:

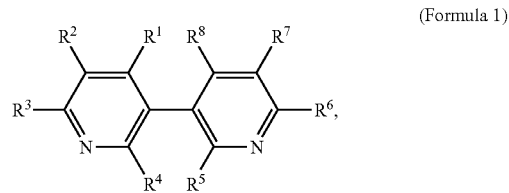

(Formula 1)

wherein $R^1$, $R^2$, $R^3$, $R^6$, $R^7$, and $R^8$ are independently selected from the group consisting of H, optionally substituted $C_{1-12}$ alkyl, optionally substituted phenyl, optionally substituted carbazolyl, optionally substituted diphenylamine, optionally substituted carbazolylphenyl, and optionally substituted diphenylaminophenyl; provided that: at least one of $R^1$, $R^2$, and $R^3$ is selected from optionally substituted carbazolyl, optionally substituted diphenylamine, optionally substituted carbazolylphenyl, and optionally substituted diphenylaminophenyl and at least one of $R^6$, $R^7$, and $R^8$ is selected from optionally substituted carbazolyl, optionally substituted diphenylamine, optionally substituted carbazolylphenyl, and optionally substituted diphenylaminophenyl; and $R^4$ and $R^5$ are independently selected from the group consisting of H, optionally substituted $C_{1-12}$ alkyl, optionally substituted phenyl, optionally substituted diphenylamine and optionally substituted diphenylaminophenyl.

In some embodiments, the compound may be further represented by Formula 2:

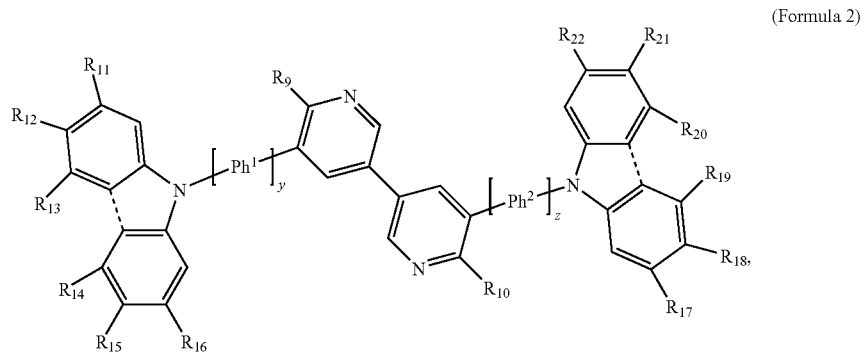

(Formula 2)

wherein each dotted line is independently an optional bond, $Ph^1$ and $Ph^2$ are independently optionally substituted 1,4-interphenylene or optionally substituted 1,3-interphenylene, y and z are independently 0 or 1; $R^9$ and $R^{10}$ are independently H, $C_{1-3}$ alkyl, or $C_{1-3}$ perfluoroalkyl; and $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently selected from the group consisting of H, $C_{1-12}$ alkyl, $C_{1-6}F_{1-13}$ fluoroalkyl, and optionally substituted phenyl.

Some embodiments also provide a compound selected from optionally substituted 5,5'-bis(diphenylamino)-3,3'-bipyridine, optionally substituted 6,6'-(dicarbazole-9-yl)-3,3'-bipyridine, optionally substituted 6,6'-bis(diphenylamino)-3,3'-bipyridine, optionally substituted 5,5'-(dicarbazole-9-yl)-3,3'-bipyridine, optionally substituted 5,5'-bis(4-diphenylaminophenyl)-3,3'-bipyridine, optionally substituted 5,5'-bis(4-(3,6-dimethylcarbazol-9-yl)phenyl)-3,3'-bipyridine, optionally substituted 5,5'-bis(4-(carbazol-9-yl)phenyl)-3,3'-bipyridine, optionally substituted 5,5'-bis(4-di(4-methylphenyl)aminophenyl)-3,3'-bipyridine, optionally substituted 4,4'-(3,3'-bipyridine-6,6'-diyl)bis(N,N-diphenylaniline), optionally substituted 5,5'-bis(3-diphenylaminophenyl)-3,3'-bipyridine, optionally substituted 5,5'-bis(3-(carbazol-9-yl)phenyl)-3,3'-bipyridine, and optionally substituted 6,6'-bis(4-(carbazol-9-yl)phenyl)-3,3'-bipyridine.

Other embodiments provide an organic light-emitting diode device comprising: a cathode; an anode; and an organic component, disposed between the anode and the cathode; wherein the organic component comprises a host compound described herein.

DETAILED DESCRIPTION OF THE PREFERRED EMBODIMENT

Definitions

Figure 1:
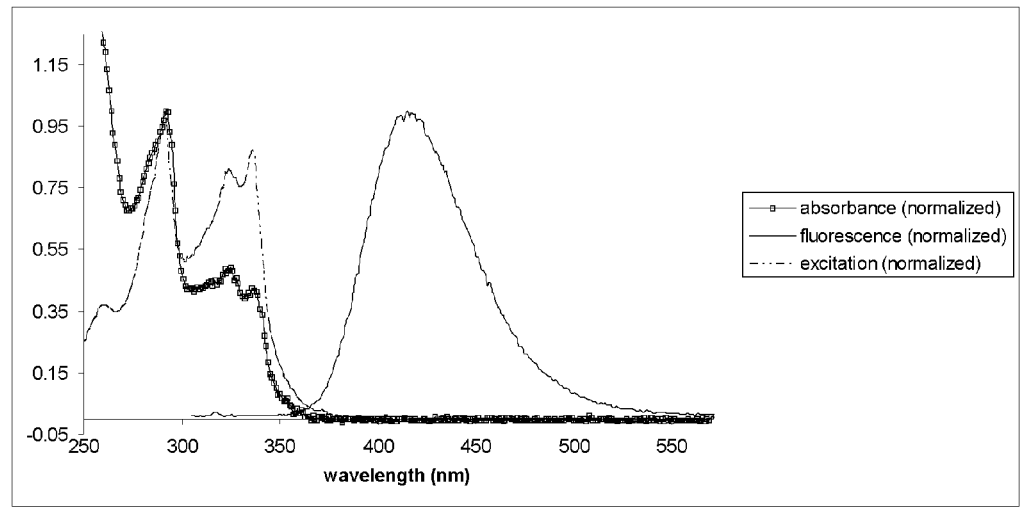
FIG. 1 displays the spectroscopic properties of one embodiment of the host compound in $CHCl_3$ solution.

As used herein, the term "alkyl" refers to a fully saturated hydrocarbon moiety. Examples include, but are not limited to, linear alkyl, branched alkyl, cycloalkyl, or combinations thereof. Alkyl may be bonded to any other number of moieties (e.g. be bonded to 1 other group, such as —$CH_3$, 2 other groups, such as —$CH_2$—, or any number of other groups) that the structure may bear, and in some embodiments, may contain from one to thirty-five carbon atoms. Examples of alkyl groups include but are not limited to $CH_3$ (e.g. methyl), $C_2H_5$ (e.g. ethyl), $C_3H_7$ (e.g. propyl isomers such as propyl, isopropyl, etc.), $C_3H_6$ (e.g. cyclopropyl), $C_4H_9$ (e.g. butyl isomers) $C_4H_8$ (e.g. cyclobutyl isomers such as cyclobutyl, methylcyclopropyl, etc.), $C_5H_{11}$ (e.g. pentyl isomers), $C_5H_{10}$ (e.g. cyclopentyl isomers such as cyclopentyl, methylcyclobutyl, dimethylcyclopropyl, etc.) $C_6H_{13}$ (e.g. hexyl isomers), $C_6H_{12}$ (e.g. cyclohexyl isomers), $C_7H_{15}$ (e.g. heptyl isomers), $C_7H_{14}$ (e.g. cycloheptyl isomers), $C_8H_{17}$ (e.g. octyl isomers), $C_8H_{16}$ (e.g. cyclooctyl isomers), $C_9H_{19}$ (e.g. nonyl isomers), $C_9H_{18}$ (e.g. cyclononyl isomers), $C_{10}H_{21}$ (e.g. decyl isomers), $C_{10}H_{20}$ (e.g. cyclodecyl isomers), $C_{11}H_{23}$ (e.g. undecyl isomers), $C_{11}H_{22}$ (e.g. cycloundecyl isomers), $C_{12}H_{25}$ (e.g. dodecyl isomers), $C_{12}H_{24}$ (e.g. cyclododecyl isomers), $C_{13}H_{27}$ (e.g. tridecyl isomers), $C_{13}H_{26}$ (e.g. cyclotridecyl isomers), and the like.

Alkyl may also be defined by the following general formulas: the general formula for linear or branched fully saturated hydrocarbons not containing a cyclic structure is $C_nH_{2n+2}$, and the general formula for a fully saturated hydrocarbon containing one ring is $C_nH_{2n}$. A $C_{X-Y}$ alkyl or $C_X$-$C_Y$ alkyl is an alkyl having from X to Y carbon atoms. For example, $C_{1-12}$ alkyl or $C_1$-$C_{12}$ alkyl includes fully saturated hydrocarbon containing 1, 2, 3, 4, 5, 6, 7, 8, 9, 10, 11, or 12 carbon atoms.

As used herein, "optionally substituted" group refers to a group that may be substituted or unsubstituted. A substituted group is derived from the unsubstituted parent structure wherein one or more hydrogen atoms on the parent structure have been independently replaced by one or more substituent groups. A substituted group may have one or more substituent groups on the parent group structure. The substituent groups are independently selected from optionally substituted phenyl, optionally substituted alkyl, —O-alkyl (e.g. —$OCH_3$, —$OC_2H_5$, —$OC_3H_2$, —$OC_4H_9$, etc.), —S-alkyl (e.g. —$SCH_3$, —$SC_2H_5$, —$SC_3H_7$, —$SC_4H_9$, etc.), —NR'R", —OH, —SH, —CN, —$NO_2$, or a halogen, wherein R' and R" are independently H or optionally substituted alkyl. Wherever a substituent is described as "optionally substituted," that substituent can be substituted with the above substituents.

Optionally substituted alkyl refers to unsubstituted alkyl and substituted alkyl. The substituted alkyl refers to substituted alkyl where one or more H atoms are replaced by one or more substituent groups, such as —O-alkyl (e.g. —$OCH_3$, —$OC_2H_5$, —$OC_3H_7$, —$OC_4H_9$, etc.), —S-alkyl (e.g. —$SCH_3$, —$SC_2H_5$, —$SC_3H_2$, —$SC_4H_9$, etc.), —NR'R" where R' and R" are independently H or alkyl, —OH, —SH, —CN, —$NO_2$, or a halogen. Some examples of optionally substituted alkyl may be alkyl, haloalkyl, perfluoroalkyl, hydroxyalkyl, alkylthiol (i.e. alkyl-SH), -alkyl-CN, etc.

Optionally substituted $C_{1-12}$ alkyl refers to unsubstituted $C_{1-12}$ alkyl and substituted $C_{1-12}$ alkyl. The substituted $C_{1-12}$ alkyl refers to $C_{1-12}$ alkyl where one or more hydrogen atoms are independently replaced by one or more of the substituent groups indicated above.

The term "halogen" or "halo" refers to fluoro, chloro, bromo or iodo.

The term "fluoroalkyl" refers to alkyl having one or more fluorine substituents. In other words, it is substituted alkyl where one or more hydrogen atoms are substituted by fluorine, but no other atoms except C, H, and F are present. $C_{1-6}F_{1-13}$ fluoroalkyl refers to fluoroalkyl having 1-6 carbon atoms and 1-13 fluorine atoms.

The term "perfluoroalkyl" refers to fluoroalkyl with a formula $C_6F_{2n+1}$ for a linear or branched structure, e.g., $CF_3$, $C_2F_5$, $C_3F_7$, $C_4F_9$, $C_5F_{11}$, $C_6F_{13}$, etc., or $C_nF_{2n}$ for a cyclic structure, e.g., cyclic $C_3F_6$, cyclic $C_4F_8$, cyclic $C_5F_{10}$, cyclic $C_6F_{12}$, etc. In other words, every hydrogen atom in alkyl is replaced by fluorine. For example, while not intending to be limiting, $C_{1-3}$ perfluoroalkyl refers to $CF_3$, $C_2F_5$, and $C_3F_7$ isomers.

The term "optionally substituted phenyl" refers to unsubstituted phenyl or substituted phenyl. In substituted phenyl, one or more hydrogen atoms on the ring system are independently replaced by one or more substituent groups indicated above. In some embodiments, optionally substituted phenyl may be optionally substituted 1,4-interphenylene or optionally substituted 1,3-interphenylene.

The structures of some of the optionally substituted ring systems referred to herein are depicted below. These ring systems may be unsubstituted, or one or more hydrogen atoms on the ring system may be independently replaced by one or more substituent groups indicated above.

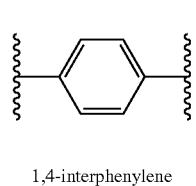
1,4-interphenylene

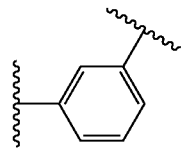
1,3-interphenylene

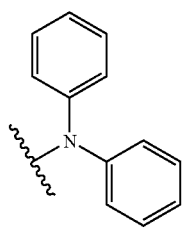
Diphenylamine

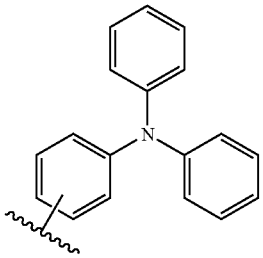
diphenylaminophenyl

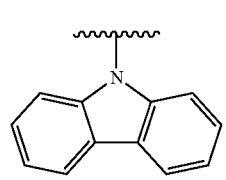
carbazolyl

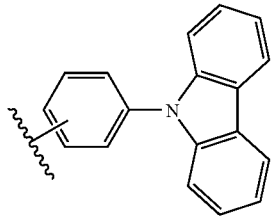
carbazolylphenyl

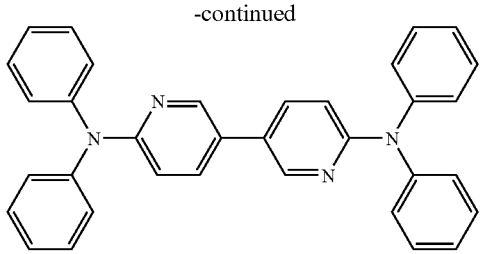
6,6'-bis(diphenylamino)-3,3'-bipyridine

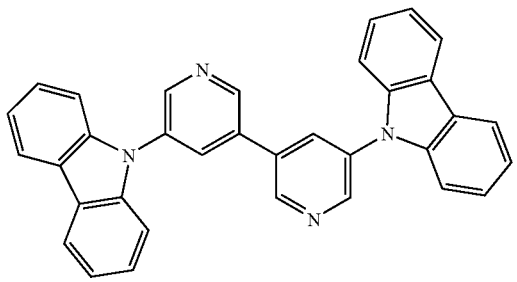
5,5'-(dicarbazole-9-yl)-3,3'-bipyridine

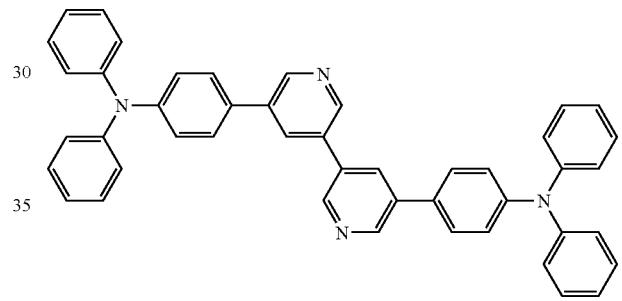
5,5'-bis(4-diphenylaminophenyl)-3,3'-bipyridine

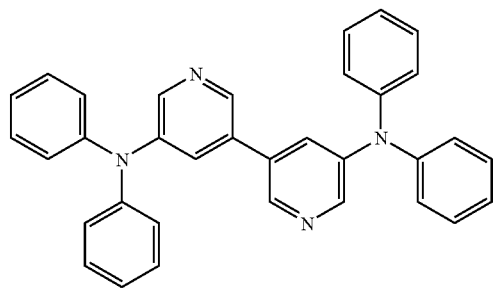
5,5'-bis(diphenylamino)-3,3'-bipyridine

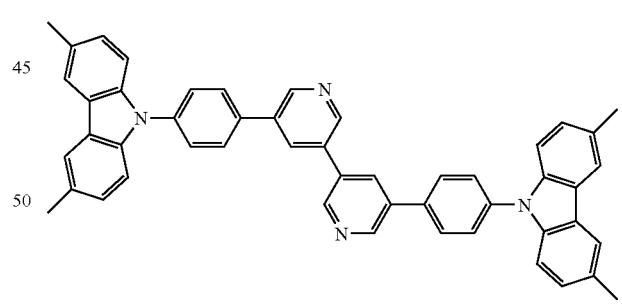
5,5'-bis(4-(3,6-dimethylcarbazol-9-yl)phenyl)-3,3'-bipyridine

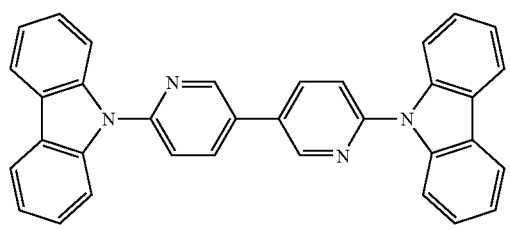
6,6'-(dicarbazole-9-yl)-3,3'-bipyridine

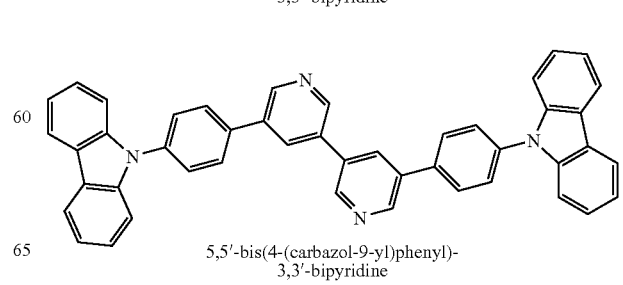
5,5'-bis(4-(carbazol-9-yl)phenyl)-3,3'-bipyridine

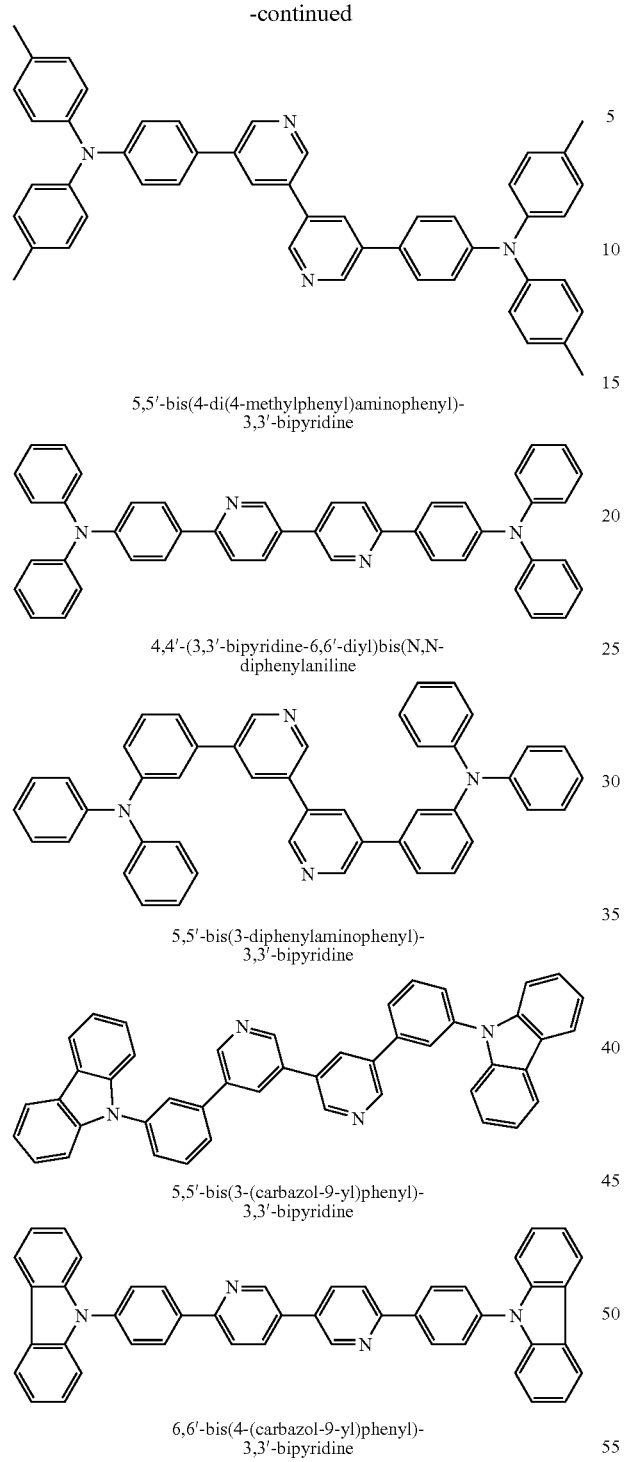

5,5'-bis(4-di(4-methylphenyl)aminophenyl)-
3,3'-bipyridine 4,4'-(3,3'-bipyridine-6,6'-diyl)bis(N,N-
diphenylaniline 5,5'-bis(3-diphenylaminophenyl)-
3,3'-bipyridine 5,5'-bis(3-(carbazol-9-yl)phenyl)-
3,3'-bipyridine 6,6'-bis(4-(carbazol-9-yl)phenyl)-
3,3'-bipyridine A "C2 symmetry axis" is an axis wherein rotating a molecule by 180° (i.e. 360°/2) about that axis yields the same structure. For example, in Formula 1, if: 1) $R^1$ is the same as $R^8$, 2) $R^2$ is the same as $R^7$, 3) $R^3$ is the same as $R^6$, and 4) $R^4$ is the same as $R^5$, then the molecule has a C2 symmetry axis.

The term "ambipolar material" refers to a material that is capable of transferring both holes and electrons effectively.

The term "phosphorescent material" refers to a material that can emit light from both singlet and triplet excitons.

The embodiments provide a compound represented by Formula 1:

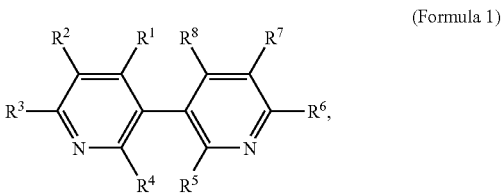

(Formula 1)

With respect to Formula 1, $R^1$, $R^2$, $R^3$, $R^6$, $R^7$, and $R^8$ are independently selected from the group consisting of H, optionally substituted $C_{1-12}$ alkyl such as optionally substituted methyl, optionally substituted ethyl, optionally substituted propyl isomers, optionally substituted cyclopropyl, optionally substituted butyl isomers, optionally substituted cyclobutyl isomers (such as cyclobutyl, methylcyclopropyl, etc.), optionally substituted pentyl isomers, optionally substituted cyclopentyl isomers, optionally substituted hexyl isomers, optionally substituted cyclohexyl isomers, optionally substituted heptyl isomers, optionally substituted cycloheptyl isomers; optionally substituted octyl isomers, optionally substituted cyclooctyl isomers, optionally substituted nonyl isomers, optionally substituted cyclononyl isomers, optionally substituted decyl isomers, optionally substituted cyclodecyl isomers, or the like; optionally substituted phenyl; optionally substituted carbazolyl; optionally substituted diphenylamine; and optionally substituted diphenylaminophenyl. In some embodiments, $R^1$, $R^2$, $R^3$, $R^6$, $R^7$, and $R^8$ are independently selected from the group consisting of H, unsubstituted $C_{1-12}$ alkyl, $C_{1-12}$ alkyl having from 1 to 13 halogen substituents (such as $CF_3$, $C_2F_5$, $C_3F_7$, $C_4F_9$, $C_5F_{11}$, $C_6F_{13}$, cyclic $C_3F_6$, cyclic $C_4F_8$, cyclic $C_5F_{10}$, cyclic $C_6F_{12}$, etc.), optionally substituted phenyl, optionally substituted carbazolyl, optionally substituted diphenylamine, optionally substituted carbazolylphenyl, and optionally substituted diphenylaminophenyl. In some embodiments, $R^1$, $R^3$, $R^4$, $R^5$, $R^6$, and $R^8$ are H, and $R^2$ and $R^7$ are independently selected from optionally substituted carbazolyl, optionally substituted diphenylamine, optionally substituted carbazolylphenyl, and optionally substituted diphenylaminophenyl.

With respect to Formula 1, at least one of $R^1$, $R^2$, and $R^3$ is selected from optionally substituted carbazolyl, optionally substituted diphenylamine, optionally substituted carbazolylphenyl, and optionally substituted diphenylaminophenyl and at least one of $R^6$, $R^7$, and $R^8$ is selected from optionally substituted carbazolyl, optionally substituted diphenylamine, optionally substituted carbazolylphenyl, and optionally substituted diphenylaminophenyl.

With respect to Formula 1, $R^4$ and $R^5$ are independently selected from the group consisting of H, optionally substituted $C_{1-12}$ alkyl, optionally substituted phenyl, optionally substituted diphenylamine and optionally substituted diphenylaminophenyl.

In Formula I, each pyridinyl ring of the bipyridine substructure has at least one optionally substituted carbazolyl, optionally substituted diphenylamine, optionally substituted carbazolylphenyl, or optionally substituted diphenylaminophenyl which is located in a position other than the ortho position between the ring nitrogen and the carbon that connects the two rings (i.e. the position of $R^4$ and $R^5$). In some embodiments, $R^2$ and $R^7$ are independently selected from optionally substituted carbazolyl, optionally substituted diphenylamine, optionally substituted carbazolylphenyl, or optionally substituted diphenylaminophenyl. In other embodiments, $R^3$ and $R^6$ are optionally substituted carbazolyl, optionally substituted diphenylamine, optionally substituted carbazolylphenyl, or optionally substituted diphenylaminophenyl.

In some embodiments, $R^2$ and $R^7$ are independently selected from optionally substituted carbazolyl, optionally substituted diphenylamine, optionally substituted carbazolylphenyl, or optionally substituted diphenylaminophenyl, and $R^1$, $R^3$, $R^6$, and $R^8$ are independently H, $C_{1-8}$ alkyl, or $C_{1-3}$ perfluoroalkyl. In other embodiments, $R^3$ and $R^6$ are optionally substituted carbazolyl, optionally substituted diphenylamine, optionally substituted carbazolylphenyl, or optionally substituted diphenylaminophenyl, and $R^1$, $R^2$, $R^7$, and $R^8$ are independently H, $C_{1-8}$ alkyl, or $C_{1-3}$ perfluoroalkyl. In other embodiments, $R^2$ and $R^7$ are selected from optionally substituted carbazolyl, optionally substituted diphenylamine, optionally substituted carbazolylphenyl, and optionally substituted diphenylaminophenyl, and $R^1$, $R^3$, $R^6$, and $R^8$ are H. In other embodiments, $R^3$ and $R^6$ are optionally substituted carbazole, and $R^1$, $R^2$, $R^7$, and $R^8$ are H. In some embodiments, $R^4$ and $R^5$ are H. In other embodiments, $R^1$, $R^3$, $R^4$, $R^5$, $R^6$, and $R^8$ are H, and $R^2$ and $R^7$ are optionally substituted carbazolyl.

In some embodiments, the optionally substituted $C_{1-12}$ alkyl is unsubstituted $C_{1-12}$ alkyl, or $C_{1-12}$ alkyl substituted by 1 to 13 halogen atoms.

In some embodiments, the compound of Formula 1 has a C2 symmetry axis. In other embodiments, the compound of Formula 1 does not have a C2 symmetry axis.

Some embodiments provide a compound represented by Formula 2:

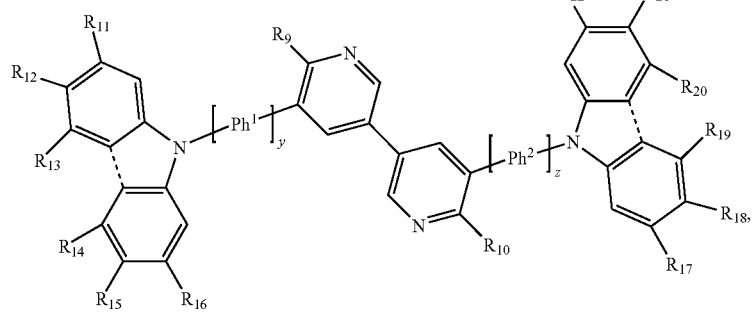

(Formula 2)

With respect to Formula 2, each dotted line is independently an optional bond. For example, some embodiments relate to compounds represented by Formula 2A or Formula 2B.

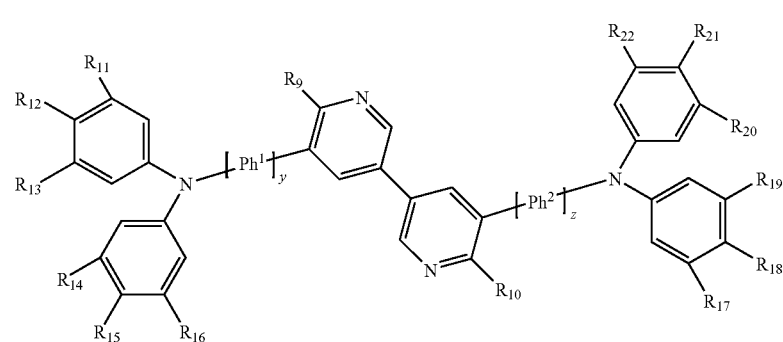

(Formula 2A)

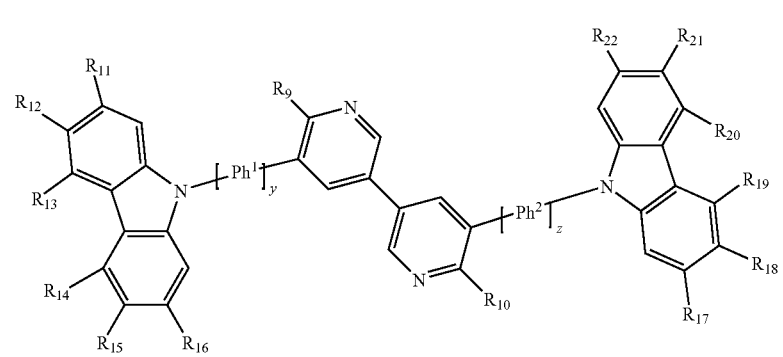

(Formula 2B)

In embodiments related to Formula 2, Formula 2A, and Formula 2B, $Ph^1$ and $Ph^2$ are independently optionally substituted 1,4-interphenylene or optionally substituted 1,3-interphenylene. In some embodiments, $Ph^1$ and $Ph^2$ may have 1, 2, or 3 substituents independently selected from $C_{1-6}$ alkyl and $C_{1-6}$ perfluoroalkyl.

Furthermore, with respect to Formula 2, Formula 2A, and Formula 2B, y may be 0 or 1 and z may be 0 or 1. $R^9$ and $R^{10}$ are independently H, $C_{1-3}$ alkyl, or $C_{1-3}$ perfluoroalkyl; and $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently selected from the group consisting of H, $C_{1-12}$ alkyl, $C_{1-6}F_{1-13}$ fluoroalkyl, and optionally substituted phenyl.

With respect to Formula 2, Formula 2A, and Formula 2B, in some embodiments, $R^9$ and $R^{10}$ are H; $R^9$ and $R^{10}$ are $CH_3$; or, alternatively, $R^9$ and $R^{10}$ are $CF_3$. In other embodiments, $R^{11}$ is $C_{1-8}$ alkyl, or alternatively, phenyl. In other embodiments, $R^{12}$ is $C_{1-8}$ alkyl, or alternatively, phenyl. In other embodiments, $R^{11}$, $R^{16}$, $R^{17}$, and $R^{22}$ are independently H or $C_{1-8}$ alkyl. In some embodiments, $R^{11}$, $R^{16}$, $R^{17}$, and $R^{22}$ are independently $C_{1-8}$ alkyl or phenyl. In some embodiments, $R^{11}$, $R^{16}$, $R^{18}$, and $R^{21}$ are independently H, $C_{1-8}$ alkyl or phenyl. In some embodiments, $R^{12}$, $R^{15}$, $R^{18}$, and $R^{21}$ are independently H, $C_{1-8}$ alkyl or phenyl.

Other embodiments provide a compound selected from optionally substituted 5,5'-bis(diphenylamino)-3,3'-bipyridine, optionally substituted 6,6'-(dicarbazole-9-yl)-3,3'-bipyridine, optionally substituted 6,6'-bis(diphenylamino)-3,3'-bipyridine, optionally substituted 5,5'-(dicarbazole-9-yl)-3,3'-bipyridine, optionally substituted 5,5'-bis(4-diphenylaminophenyl)-3,3'-bipyridine, optionally substituted 5,5'-bis(4-(3,6-dimethylcarbazol-9-yl)phenyl)-3,3'-bipyridine, optionally substituted 5,5'-bis(4-(carbazol-9-yl)phenyl)-3,3'-bipyridine, optionally substituted 5,5'-bis(4-di(4-methylphenyl)aminophenyl)-3,3'-bipyridine, optionally substituted 4,4'-(3,3'-bipyridine-6,6'-diyl)bis(N,N-diphenylaniline), optionally substituted 5,5'-bis(3-diphenylaminophenyl)-3,3'-bipyridine, optionally substituted 5,5'-bis(3-(carbazol-9-yl)phenyl)-3,3'-bipyridine, and optionally substituted 6,6'-bis(4-(carbazol-9-yl)phenyl)-3,3'-bipyridine. In some embodiments, these compounds may be unsubstituted, or have 1, 2, 3, 4, 5, or 6 substituents independently selected from: $C_{1-12}$ alkyl; $CF_3$; and phenyl having 0, 1, or 2 substituents, wherein the substituents on phenyl are independently $C_{1-3}$ alkyl or $CF_3$.

Some embodiments provide a compound represented by Formula 3:

(Formula 3)

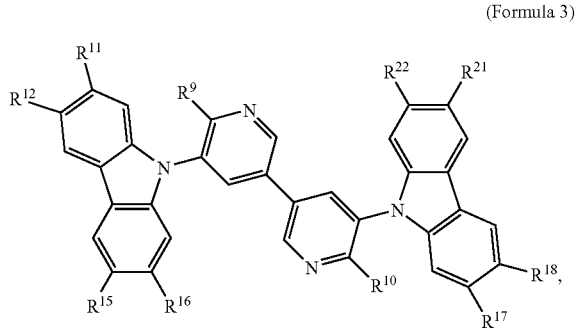

wherein $R^9$ and $R^{10}$ are independently H, $CH_3$, or $CF_3$; and $R^{11}$, $R^{12}$, $R^{15}$, $R^{16}$, $R^{17}$, $R^{18}$, $R^{21}$, and $R^{22}$ are independently H, unsubstituted phenyl, or $C_{1-8}$ alkyl. In some embodiments, $R^{11}$, $R^{16}$, $R^{17}$, and $R^{22}$ are independently H, $C_{1-8}$ alkyl, or phenyl. In other embodiments, $R^{11}$, $R^{16}$, $R^{18}$, and $R^{21}$ are independently H, $C_{1-8}$ alkyl or phenyl. In other embodiments, $R^{12}$, $R^{15}$, $R^{18}$, and $R^{21}$ are independently H, $C_{1-8}$ alkyl or phenyl.

Some embodiments provide one of the compounds below.

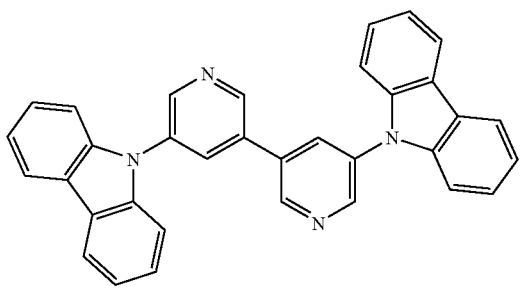

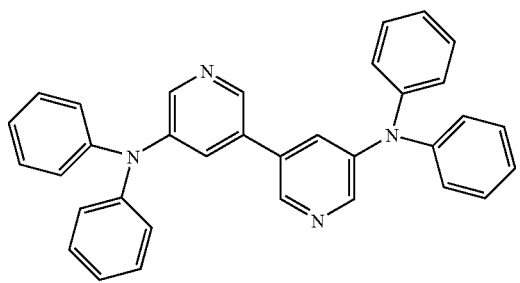

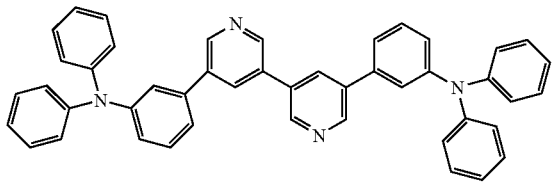

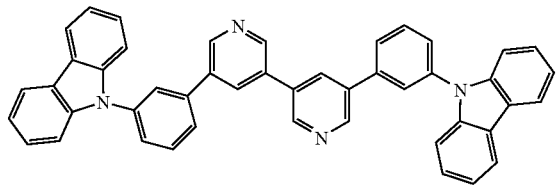

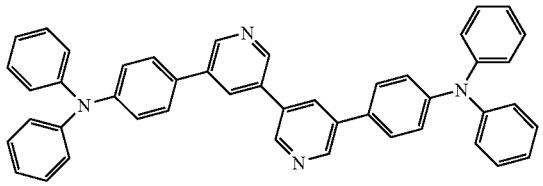

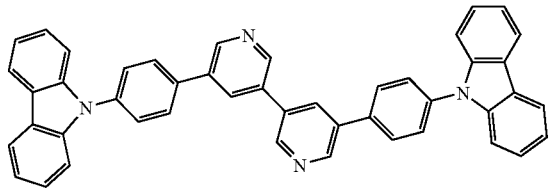

-continued

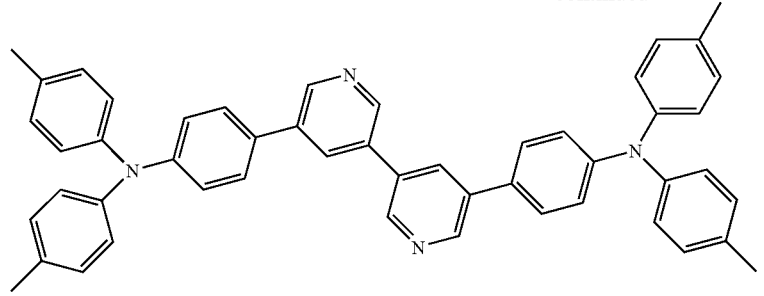

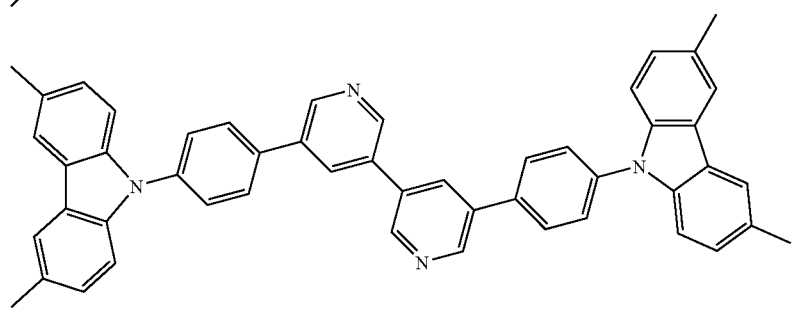

The compounds described herein can be incorporated into light-emitting devices in various ways. A light-emitting device may have a cathode, an anode, and an organic component comprising a compound described herein. At least one of the compounds described herein may be present in the organic component, and may be useful as a host material with electron-transfer properties, hole-transfer properties, or both electron-transfer and hole-transfer properties.

In some embodiments, the organic component comprises a light-emitting layer, and the device may be configured to allow holes to be transported from the anode to the light-emitting layer and allow electrons to be transported from the cathode to the light-emitting layer. The light-emitting layer may optionally comprise the host compound. Additionally, the organic component may further comprise a hole-transport layer disposed between the anode and the light-emitting layer, and which may be configured to allow holes to be transported from the anode to the light-emitting layer. The organic component may further comprise an electron-transport layer disposed between the cathode and the light-emitting layer, which may be configured to allow electrons to be transported from the cathode to the light-emitting layer.

In some embodiments, at least one of the light-emitting layer, the hole-transport layer and the electron-transport layer comprise the host compound. In some embodiments, all of the light-emitting layer, the hole-transport layer and the electron-transport layer comprise the host compound. In one embodiment, the host is ambipolar, and its ability to transfer holes is about equal to its ability to transport electrons.

An anode layer may comprise a conventional material such as a metal, mixed metal, alloy, metal oxide or mixed-metal oxide, or a conductive polymer. Examples of suitable metals include the Group 1 metals, the metals in Groups 4, 5, 6, and the Group 8-10 transition metals. If the anode layer is to be light-transmitting, mixed-metal oxides of Group 12, 13, and 14 metals or alloys thereof, such as Au, Pt, and indium-tin-oxide (ITO), may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the light-emitting layer may further comprise a light-emitting component or compound. The light-emitting component may be a fluorescent and/or a phosphorescent compound. In some embodiments, the light-emitting component comprises a phosphorescent material.

The light-emitting component or compound may be chosen to vary the color of the light emitted by the light-emitting device. For example, a blue light-emitting component may emit a combination of visible photons so that the light appears to have a blue quality to an observer. In some embodiments, a blue light-emitting component may emit visible photons having an average wavelength in the range of about 440 nm or about 460 nm to about 490 nm or about 500 nm. Some non-limiting examples of compounds which may form part or all of a blue light-emitting component include iridium coordination compounds such as: bis-{2-[3,5-bis(trifluoromethyl)phenyl]pyridinato-N,C2'}iridium(III)-picolinate, bis (2-[4,6-difluorophenyl]pyridinato-N,C2')iridium (III) picolinate, bis(2-[4,6-difluorophenyl]pyridinato-N,C2')iridium(acetylacetonate), Iridium (III) bis(4,6-difluorophenylpyridinato)-3-(trifluoromethyl)-5-(pyridine-2-yl)-1,2,4-triazolate, Iridium (III) bis(4,6-difluorophenylpyridinato)-5-(pyridine-2-yl)-1H-tetrazolate, bis[2-(4,6-difluorophenyl) pyridinato-N,C2']iridium(III) tetra(1-pyrazolyl)borate, etc.

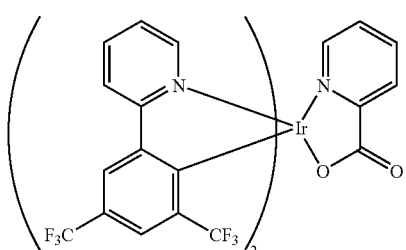

bis-{2-[3,5-bis(trifluoromethyl)phenyl]pyridinato-N,C2'}iridium(III)-picolinate (Ir(CF₃ppy)₂(Pic))

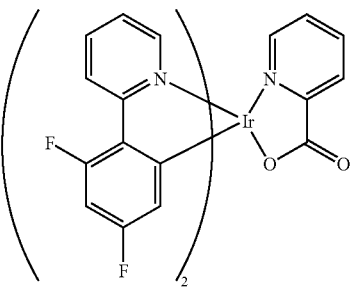

bis(2-[4,6-difluorophenyl]pyridinato-N,C2')iridium (III) picolinate [FIrPic]

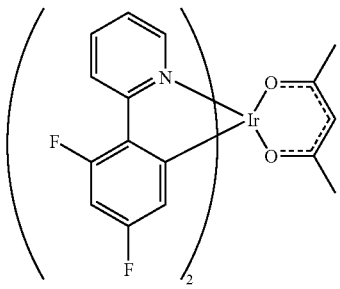

bis-(2-[4,6-difluorophenyl]pyridinato-N,C2')iridium(acetylacetonate) [FIr(acac)]

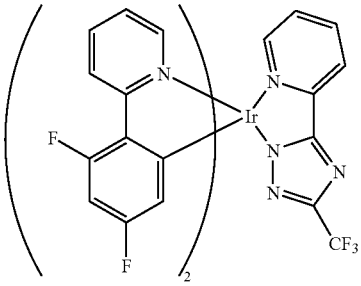

Iridium (III) bis(4,6-difluorophenylpyridinato)-3-(trifluoromethyl)-5-(pyridine-2-yl)-1,2,4-triazolate (FIrtaz)

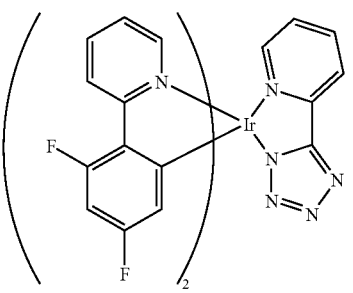

Iridium (III) bis(4,6-difluorophenylpyridinato)-5-(pyridine-2-yl)-1H-tetrazolate (FIrN4)

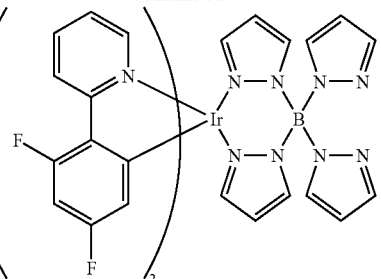

bis[2-(4,6-difluorophenyl)pyridinato-N,C2']iridium(III)tetra(1-pyrazolyl)borate (Fir6)

A red light-emitting component may emit a combination of visible photons so that the light appears to have a red quality to an observer. In some embodiments, a red light-emitting component may emit visible photons having an average wavelength in the range of about 600 nm or about 620 nm to about 780 nm or about 800 nm. Some non-limiting examples of compounds which may form part or all of a red light-emitting component include iridium coordination compounds such as: Bis[2-(2'-benzothienyl)-pyridinato-N,C3'] iridium (III)(acetylacetonate); Bis[(2-phenylquinolyl)-N,C2']iridium (III) (acetylacetonate); Bis[(1-phenylisoquinolinato-N,C2')]iridium (III) (acetylacetonate); Bis[(dibenzo[f,h]quinoxalino-N,C2')iridium (III)(acetylacetonate); Tris(2,5-bis-2'-(9',9'-dihexylfluorene)pyridine)iridium (III); Tris[1-phenylisoquinolinato-N,C2']iridium (III); Tris-[2-(2'-benzothienyl)-pyridinato-N,C3']iridium (III); Tris[1-thiophen-2-ylisoquinolinato-N,C3']iridium (III); and Tris[1-(9,9-dimethyl-9H-fluoren-2-yl)isoquinolinato-(N,C3')iridium (III)), etc.

1

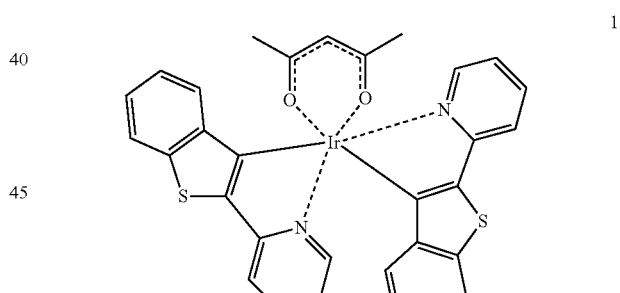

Ir(btp)₂(acac)

2

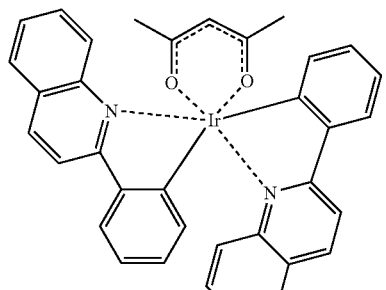

Ir(pq)₂(acac)

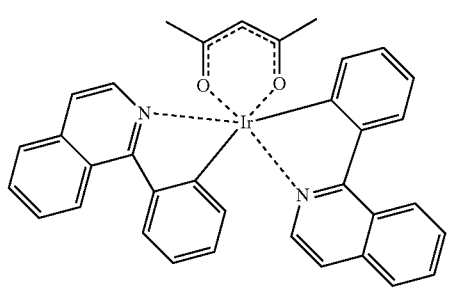

Ir(piq)₂(acac)

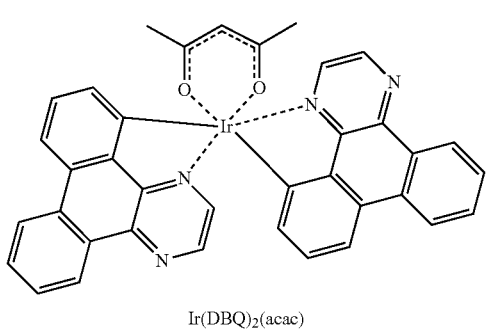

Ir(DBQ)₂(acac)

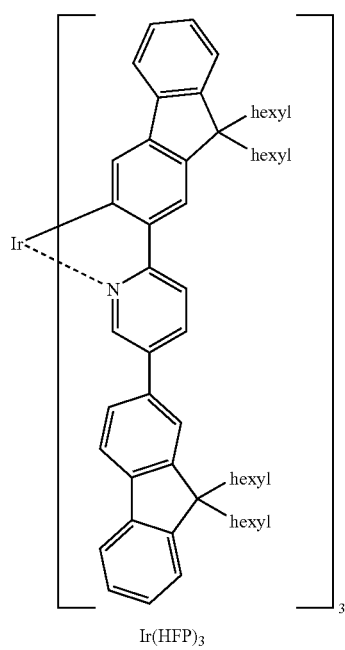

Ir(HFP)₃

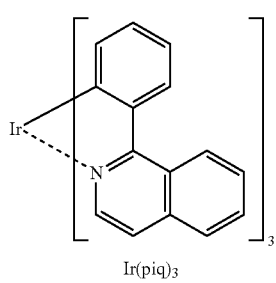

Ir(piq)₃

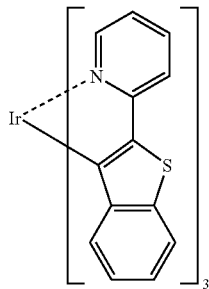

Ir(btp)₃

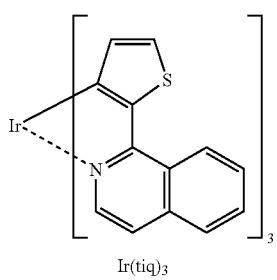

Ir(tiq)₃

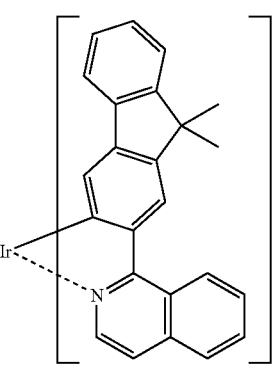

Ir(flil)₃

1. (Btp)₂Ir(III)(acac); Bis[2-(2'-benzothienyl)-pyridinato-N,C3'] iridium (III)(acetylacetonate)
2. (Pq)₂Ir(III)(acac); Bis[(2-phenylquinolyl-N,C2']iridium (III) (acetylacetonate)
3. (Piq)₂Ir(III)(acac); Bis[(1-phenylisoquinolinato-N,C2')]iridium (III) (acetylacetonate)
4. (DBQ)₂Ir(acac); Bis[(dibenzo[f, h]quinoxalino-N,C2')iridium (III) (acetylacetonate)
5. [Ir(HFP)₃], Tris(2,5-bis-2'-(9',9'-dihexylfluorene)pyridine)iridium (III)
6. Ir(piq)₃; Tris[1-phenylisoquinolinato-N,C2']iridium (III)
7. Ir(btp)₃; Tris-[2-(2'-benzothienyl)-pyridinato-N,C3'] iridium (III)
8. Ir(tiq)₃, Tris[1-thiophen-2-ylisoquinolinato-N,C3']iridium (III)
9. Ir(fliq)₃; Tris[1-(9,9-dimethyl-9H-fluoren-2-yl)isoquinolinato-(N,C3') iridium (III))

A green light-emitting component may emit a combination of visible photons so that the light appears to have a green quality to an observer. In some embodiments, a green light-emitting component may emit visible photons having an average wavelength in the range of about 490 nm or about 500 nm to about 570 nm or about 600 nm. Some non-limiting examples of compounds which may form part or all of a green light-emitting component include iridium coordination compounds such as: Bis(2-phenylpyridinato-N,C2')iridium(III) (acetylacetonate) [Ir(ppy)₂(acac)], Bis(2-(4-tolyl)pyridinato-N,C2')iridium(III)(acetylacetonate) [Ir(mppy)₂(acac)], Bis(2-(4-tert-butyl)pyridinato-N,C2')iridium (III) (acetylacetonate) [Ir(t-Buppy)₂(acac)], Tris(2-phenylpyridinato-N,C2')iridium (III) [Ir(ppy)₃], Bis(2- phenyloxazolinato-N,C2')iridium (III) (acetylacetonate) [Ir(op)₂(acac)], Tris(2-(4-tolyl)pyridinato-N,C2')iridium(III) [Ir(mppy)₃], etc.

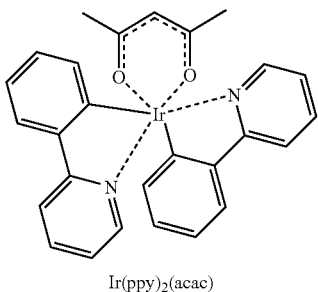

Ir(ppy)₂(acac)

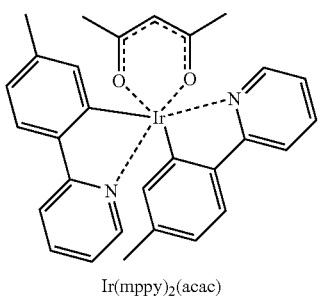

Ir(mppy)₂(acac)

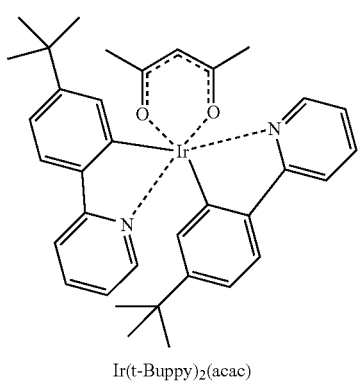

Ir(t-Buppy)₂(acac)

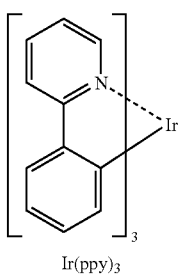

Ir(ppy)₃

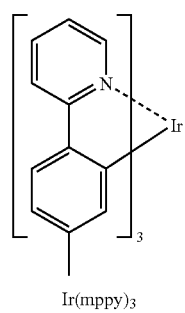

Ir(mppy)₃

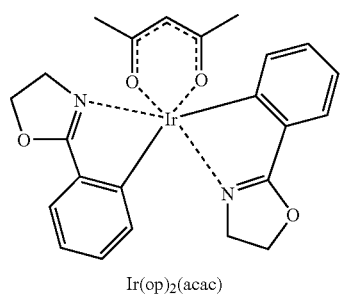

Ir(op)₂(acac)

An orange light-emitting component may emit a combination of visible photons so that the light appears to have a orange quality to an observer. In some embodiments, an orange light-emitting component may emit visible photons having an average wavelength in the range of about 570 nm or about 585 nm to about 620 nm or about 650 nm. Some non-limiting examples of compounds which may form part or all of an orange light-emitting component include iridium coordination compounds such as: Bis[2-phenylbenzothiazolato-N,C2']iridium (III)(acetylacetonate), Bis[2-(4-tert-butylphenyl)benzothiazolato-N,C2']iridium(III)(acetylacetonate), Bis[(2-(2'-thienyl)pyridinato-N,C3')]iridium (III) (acetylacetonate), Tris[2-(9.9-dimethylfluoren-2-yl)pyridinato-(N,C3')]iridium (III), Tris[2-(9.9-dimethylfluoren-2-yl)pyridinato-(N,C3')]iridium (III), Bis[5-trifluoromethyl-2-[3-(N-phenylcarbzolyl)pyridinato-N,C2']iridium(III) (acetylacetonate), (2-PhPyCz)₂Ir(III)(acac), etc.

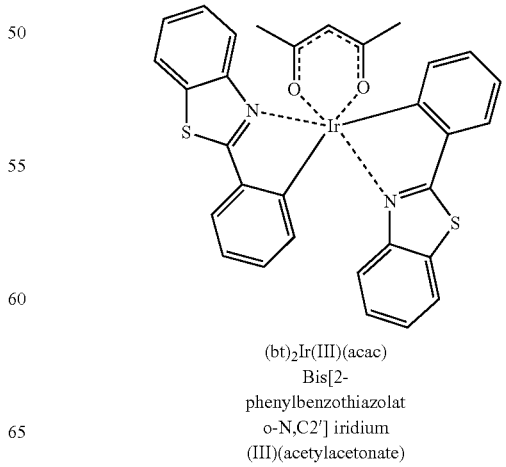

(bt)₂Ir(III)(acac)
Bis[2-phenylbenzothiazolato-N,C2'] iridium (III)(acetylacetonate)

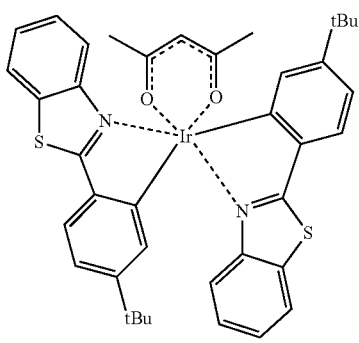

(t-bt)₂Ir(III)(acac)
Bis[2-(4-tert-
butylphenyl)benzothiazolato-
N,C2']iridium(III)(acetylacetonate)

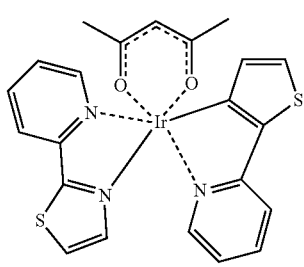

(thp)₂Ir(III)(acac)
Bis[(2-(2'-
thienyl)pyridinato-
N,C3')]iridium (III)
(acetylacetonate)

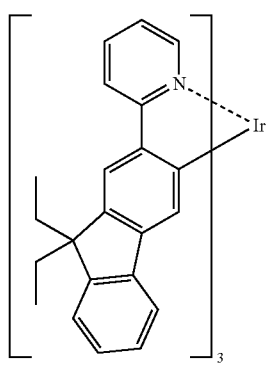

[Ir(Flpy)₃]
Tris[2-(9,9-
dimethylfluoren-2-
yl)pyridinato-
(N,C3')]iridium (III)

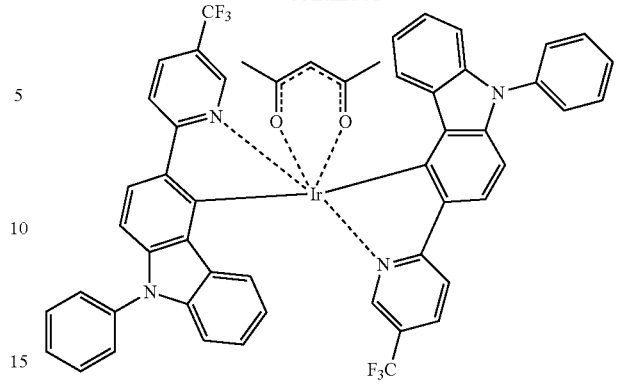

(Cz-CF₃)Ir(III)(acac)
Bis[5-trifluoromethyl-2-[3-(N-
phenylcarbzoly)pyridinato-
N,C2']iridium(III)(acetylacetonate)

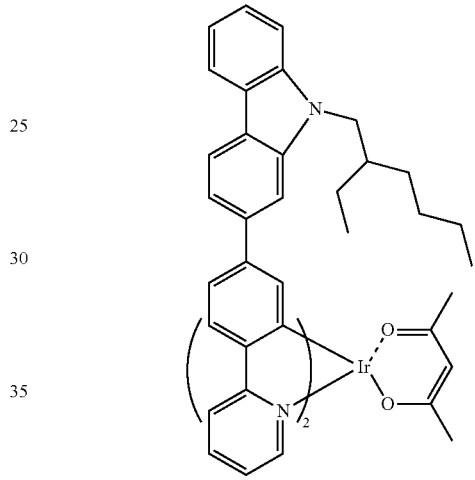

(2-PhPyCz)₂Ir(III)(acac)

A white light-emitting component may emit a combination of visible photons so that the light appears to have a white quality to an observer. There are several types of compounds which might emit white light. For example, in some embodiments a single compound may have multiple emissive moieties which independently emit different colored light. In some single compounds comprising multiple emissive moieties, the emissive moieties may be covalently combined, such as in the examples below:

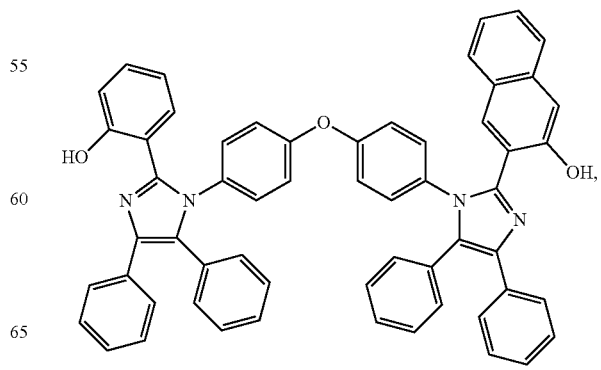

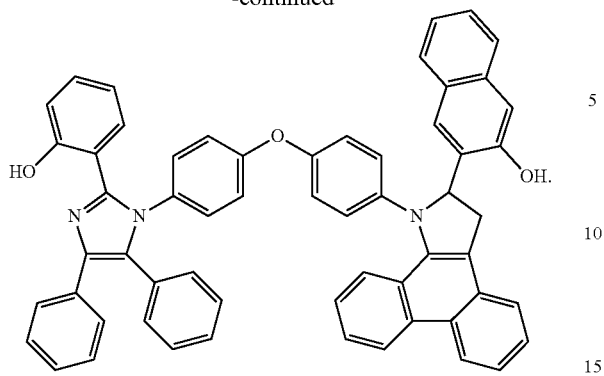

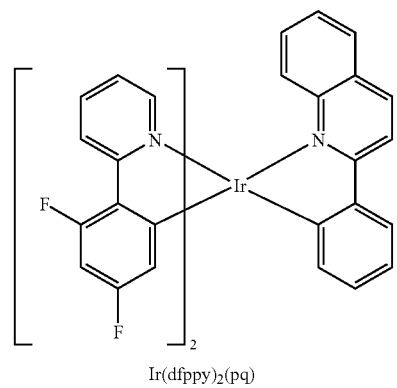

Ir(dfppy)₂(pq)

Some single compounds comprising multiple emissive moieties may be metal coordination compounds, such as iridium or platinum coordination compounds, which have at least two different ligands. These ligands may have similar lifetimes so that at least two different colors of light may be simultaneously emitted from the same compound. The compound below is an example of such a compound Another type of single compound which may emit white light is a compound that can form excimers. For these types of compounds, the monomers and excimers may emit at different wavelengths, and may thus provide two different colors of emission which together may appear white light. Some examples of such compounds are depicted below.

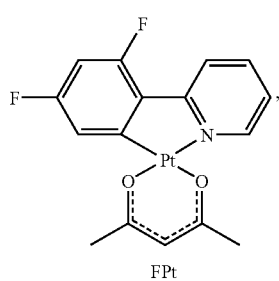

FPt

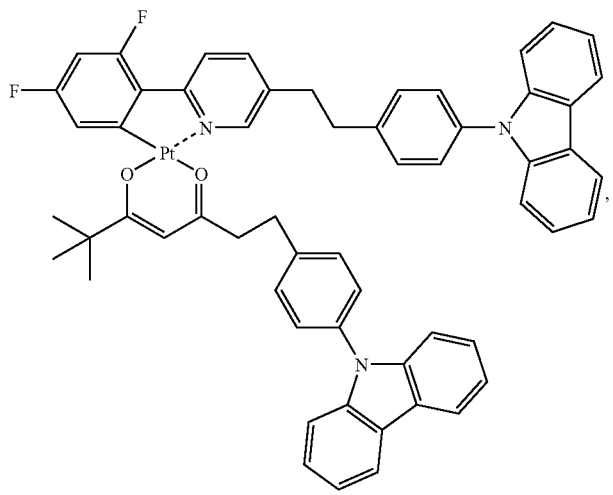

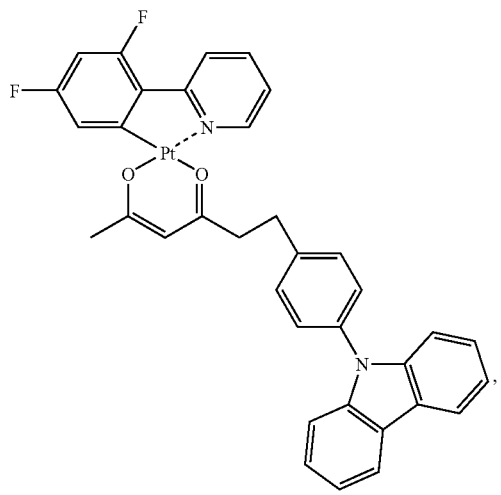

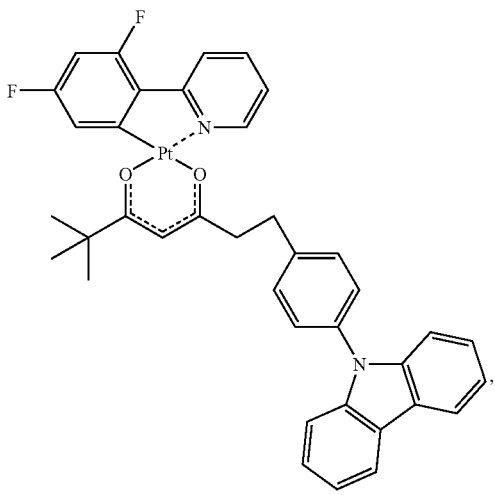

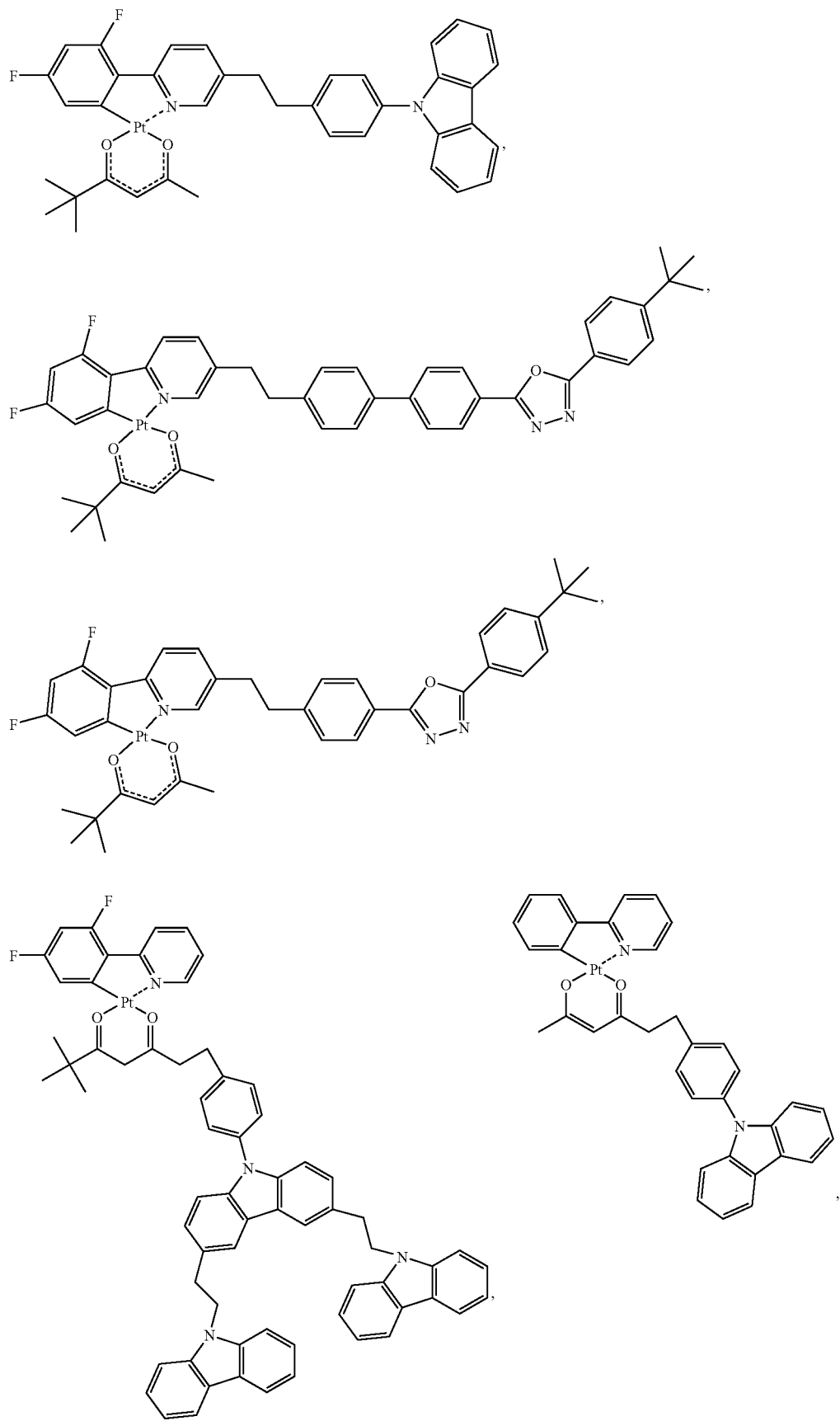

-continued
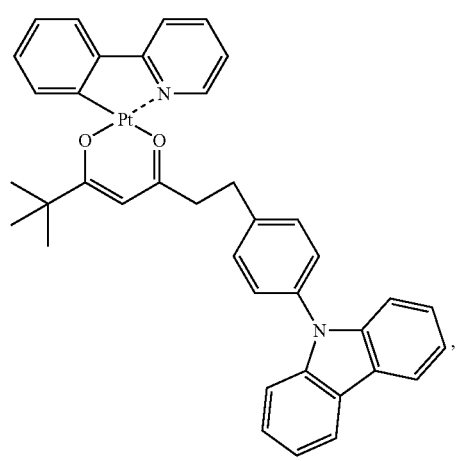
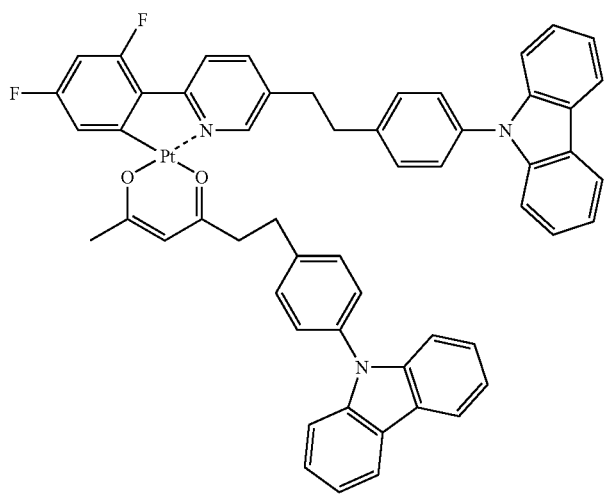
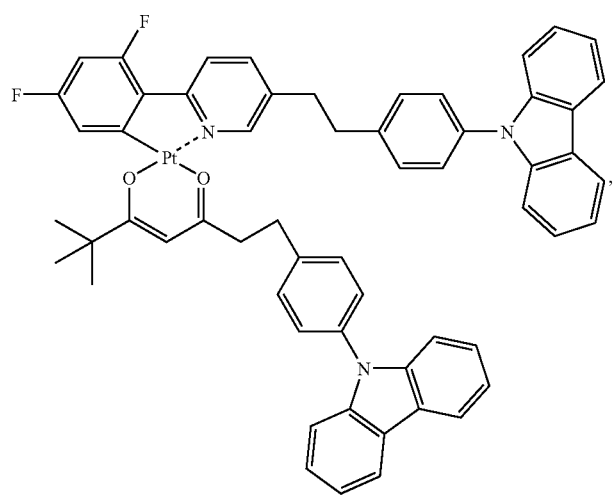
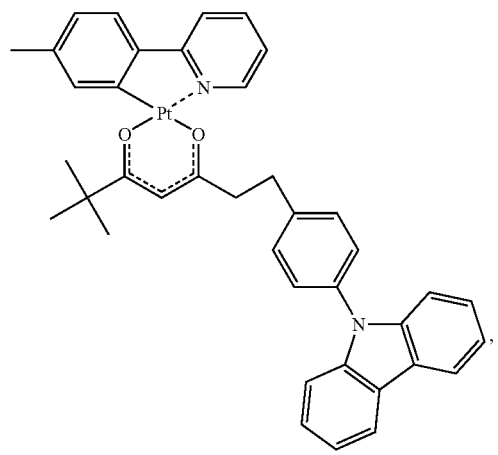
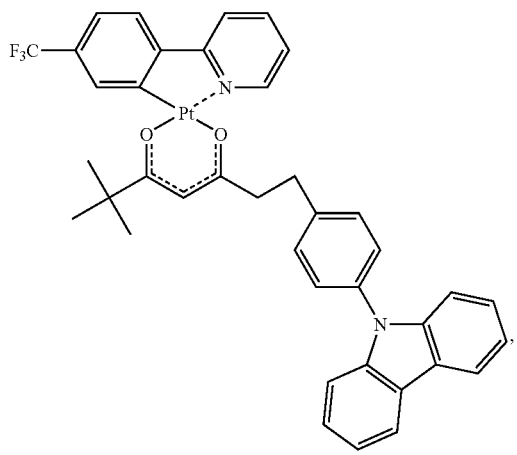

-continued

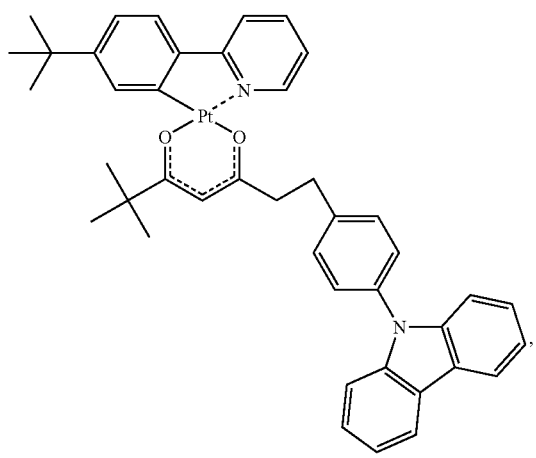

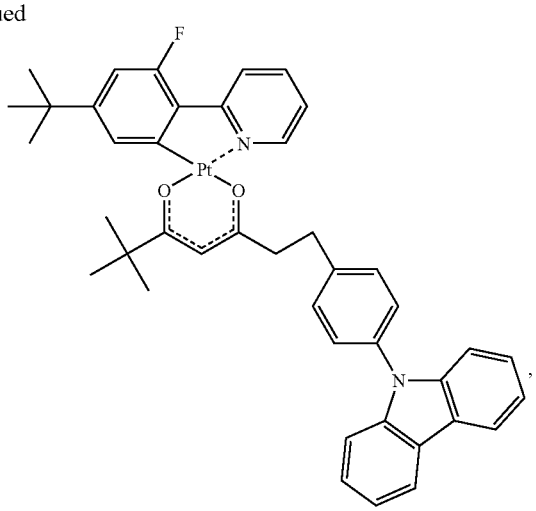

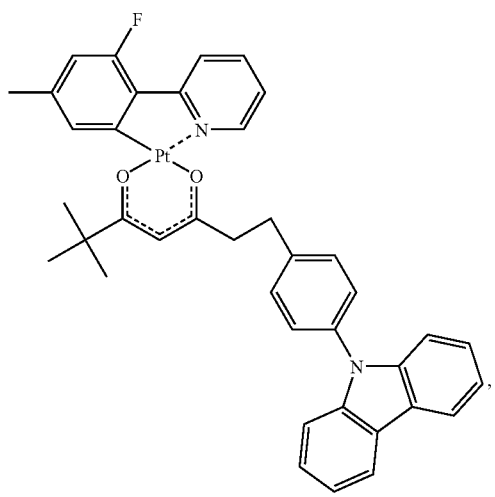 and

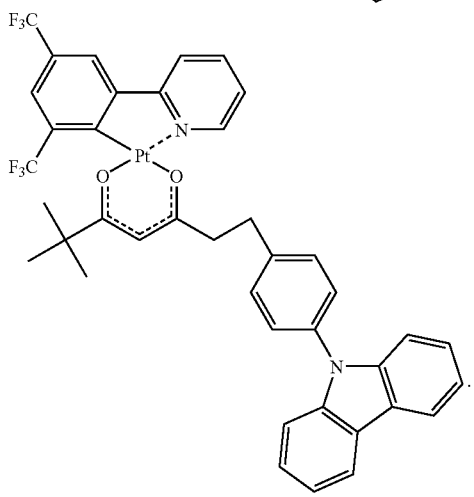

Compounds may also emit white light by other methods, for example, a single compound may form an exciplex with adjacent layer compounds, which may result in white light emission for the device. A non-limiting example of such a compound is depicted below.

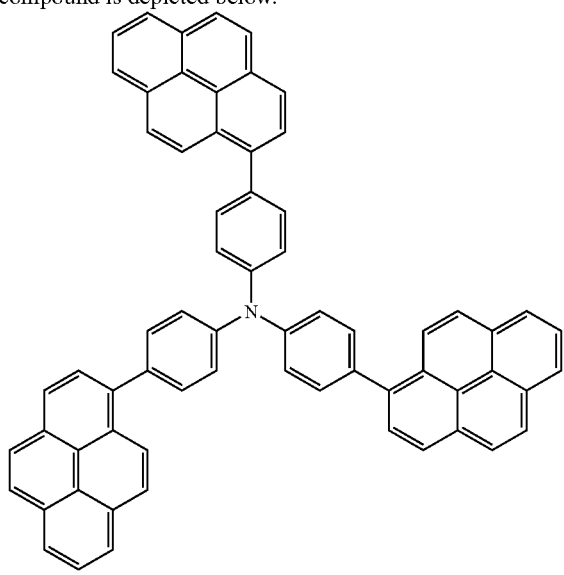

White light may also be obtained by combining, either in a single layer or in multiple layers, at least two light-emitting components having different color emission. For example, a combination of a red light-emitting component, a blue light-emitting component, and a green light-emitting component, either in a single layer or in more than one layer, may provide white light. Alternatively a combination of a blue light-emitting component, and an orange light-emitting component, either in a single layer or in more than one layer, may provide white light.

The amount of the light-emitting component may vary. In some embodiments, the light-emitting component may be about 0.1% (w/w) to about 5% (w/w), or about 1% (w/w) with respect to the host.

The thickness of the light-emitting layer may vary. In some embodiments, the light-emitting layer has a thickness from about 1 nm to about 200 nm. In some embodiments, the light-emitting layer has a thickness in the range of about 1 nm to about 100 nm.

In some embodiments, the light-emitting layer can further include additional host material. Exemplary host materials are known to those skilled in the art. For example, the host material included in the light-emitting layer can be an optionally substituted compound selected from: an aromatic-substituted amine, an aromatic-substituted phosphine, a thiophene, an oxadiazole, 2-(4-biphenyl)-5-(4-tert-butylphenyl)-1,3,4- oxadiazole (PBD), 1,3-bis(N,N-t-butyl-phenyl)-1,3,4-oxadiazole (OXD-7), a triazole, 3-phenyl-4-(1'-naphthyl)-5-phenyl-1,2,4-triazole (TAZ), 3,4,5-Triphenyl-1,2,3-triazole, 3,5-Bis(4-tert-butyl-phenyl)-4-phenyl[1,2,4]triazole, an aromatic phenanthroline, 2,9-dimethyl-4,7-diphenyl-phenanthroline (bathocuproine or BCP), 2,9-Dimethyl-4,7-diphenyl-1,10-phenanthroline, a benzoxazole, a benzothiazole, a quinoline, aluminum tris(8-hydroxyquinolate) (Alq3), a pyridine, a dicyanoimidazole, cyano-substituted aromatic, 1,3,5-tris(2-N-phenylbenzimidazolyl)benzene (TPBI), 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)-amino]-3,3'-dimethylbiphenyl (M14), 4,4'-bis[N,N'-(3-tolyl)amino]-3,3'-dimethylbiphenyl (HMTPD), 1,1-Bis(4-bis(4-methylphenyl)aminophenyl)cyclohexane, a carbazole, 4,4'-N,N'-dicarbazole-biphenyl (CBP), poly(9-vinylcarbazole) (PVK), N,N'N"-1,3,5-tricarbazoloylbenzene (tCP), a polythiophene, a benzidine, N,N'-bis(4-butylphenyl)-N,N'-bis(phenyl)benzidine, a triphenylamine, 4,4',4"-Tris(N-(naphthylen-2-yl)-N-phenylamino)triphenylamine, 4,4',4"-tris(3-methylphenylphenylamino)triphenylamine (MTDATA), a phenylenediamine, a polyacetylene, and a phthalocyanine metal complex.

In some embodiments, the light-emitting device may further comprise a hole-transport layer between the anode and the light-emitting layer and an electron-transport layer between the cathode and the light-emitting layer. In some embodiments, all of the light-emitting layer, the hole-transport layer and the electron-transport layer comprise the host compound described herein.

In some embodiments, the hole-transport layer may comprise at least one hole-transport materials. Suitable hole-transport materials are known to those skilled in the art. Exemplary hole-transport materials include: 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4"-Tris(N-(naphthylen-2-yl)-N-phenylamino)triphenylamine; 4,4',4'-tris(3-methylphenylphenylamino)triphenylamine (MTDATA); 4,4'-bis[N-(naphthyl)-N-phenyl-amino]biphenyl (α-NPD); 4,4'-bis[N,N'-(3-tolyl)amino]-3,3'-dimethylbiphenyl (HMTPD); 4,4'-bis[N,N'-(3-tolyl)amino]-3,3'-dimethylbiphenyl (M14); 4,4'-N,N'-dicarbazole-biphenyl (CBP); 1,3-N,N-dicarbazole-benzene (mCP); poly(9-vinylcarbazole) (PVK); a benzidine; a carbazole; a phenylenediamine; a phthalocyanine metal complex; a polyacetylene; a polythiophene; a triphenylamine; an oxadiazole; copper phthalocyanine; N,N'-bis(3-methylphenyl)N,N'-diphenyl-[1,1'-biphenyl]-4,4'-diamine (TPD); N,N'N"-1,3,5-tricarbazoloylbenzene (tCP); N,N'-bis(4-butylphenyl)-N,N'-bis(phenyl)benzidine; and the like.

In some embodiments, the electron-transport layer may comprise at least one electron-transport materials. Suitable electron transport materials are known to those skilled in the art. Exemplary electron transport materials that can be included in the electron transport layer are an optionally substituted compound selected from: aluminum tris(8-hydroxyquinolate) (Alq3), 2-(4-biphenyl)-5-(4-tert-butylphenyl)-1,3,4-oxadiazole (PBD), 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene (BPY-OXD), 3-phenyl-4-(1'-naphthyl)-5-phenyl-1,2,4-triazole (TAZ), 2,9-dimethyl-4,7-diphenyl-phenanthroline (bathocuproine or BCP), and 1,3,5-tris[2-N-phenylbenzimidazol-z-yl]benzene (TPBI). In one embodiment, the electron transport layer is aluminum quinolate (Alq$_3$), 2-(4-biphenyl)-1)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional materials may be included in the light-emitting device. Additional materials that may be included include an electron injection materials, hole blocking materials, exciton blocking materials, and/or hole injection materials. The electron injection materials, hole blocking materials, exciton blocking materials, and/or hole injection materials may be incorporated into any of the layers described above, or may be incorporated into one or more separate layers, such as an electron injection layer, a hole blocking layer, an exciton blocking layer, and/or a hole injection layer.

In some embodiments, the light-emitting device can include an electron injection layer between the cathode layer and the light emitting layer. In some embodiments, the lowest unoccupied molecular orbital (LUMO) energy level of the electron injection material(s) is high enough to prevent it from receiving an electron from the light emitting layer. In other embodiments, the energy difference between the LUMO of the electron injection material(s) and the work function of the cathode layer is small enough to allow efficient electron injection from the cathode. A number of suitable electron injection materials are known to those skilled in the art. Examples of suitable electron injection material(s) include but are not limited to, an optionally substituted compound selected from the following: aluminum quinolate (Alq$_3$), 2-(4-biphenyl)-1)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injection layer is aluminum quinolate (Alq$_3$), 2-(4-biphenyl)-1)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device can include a hole blocking layer, e.g., between the cathode and the light-emitting layer. Various suitable hole blocking materials that can be included in the hole blocking layer are known to those skilled in the art. Suitable hole blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton blocking layer, e.g., between the light-emitting layer and the anode. In one embodiment, the band gap of the exciton blocking material(s) is large enough to substantially prevent the diffusion of excitons. A number of suitable exciton blocking materials that can be included in the exciton blocking layer are known to those skilled in the art. Examples of exciton blocking material(s) include an optionally substituted compound selected from the following: aluminum quinolate (Alq$_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole injection layer, e.g., between the light-emitting layer and the anode. Various suitable hole injection materials that can be included in the hole injection layer are known to those skilled in the art. Exemplary hole injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenyl-benzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper. Hole-injection materials, while still being able to transport holes, may have a hole mobility substantially less than the hole mobility of conventional hole transport materials.

Those skilled in the art would recognize that the various materials described above can be incorporated in several different layers depending on the configuration of the device. In one embodiment, the materials used in each layer are selected to result in the recombination of the holes and electrons in the light-emitting layer.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein can be deposited on the anode. The cathode layer, comprising a low work functioning metal (e.g., Mg:Ag), can then be vapor evaporated onto the light-emitting layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

EXAMPLE 1

An example of the host compound may be synthesized according to the following scheme:

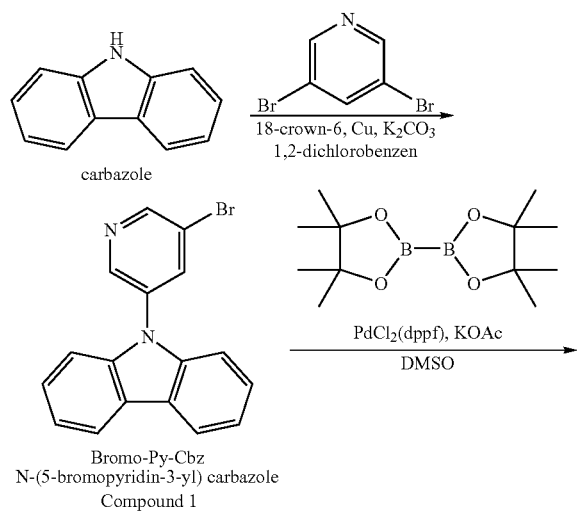

Bromo-Py-Cbz
N-(5-bromopyridin-3-yl) carbazole
Compound 1

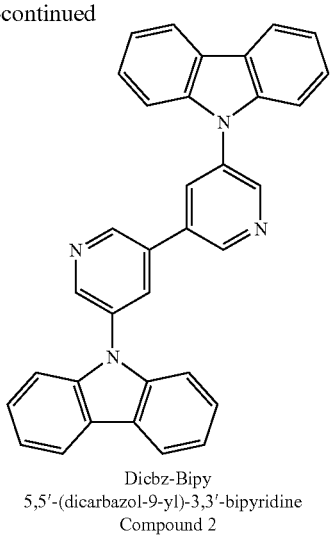

Dicbz-Bipy
5,5'-(dicarbazol-9-yl)-3,3'-bipyridine
Compound 2

Experimental

Bromo-Py-Cbz (1). Compound 1 was made according to a procedure adapted from Hou, Z.; Liu, Y.; Nishiura, M.; Wang, Y. *J. Am. Chem. Soc.* 2006, 128(17), 5592-5593. A mixture of carbazole (4.751 g, 28.41 mmol), 3,5-dibromopyridine (20.19 g, 85.23 mmol), $K_2CO_3$ (15.71 g, 113.6 mmol), copper powder (1.204 g, 18.94 mmol), 18-crown-6 ether (2.503 g, 9.470 mmol) and 1,2-dichlorobenzene (150 mL) was degassed with argon for 1 h while stirring. The reaction mixture was then maintained at 200° C. with stirring under argon for 20 h. Upon cooling to RT, the crude mixture was filtered and concentrated in vacuo. The resulting residue was then purified by flash chromatography ($SiO_2$, 1:1 to 11:9 dichloromethane-hexanes) to afford 1 (6.75 g, 74%) as a white solid: mp=118-120° C.; $^1$H NMR (400 MHz, $CDCl_3$): δ 8.81 (dd, J=23.2, 2.0 Hz, 2H), 8.14 (d, J=7.7 Hz, 2H), 8.10 (t, J=2.2 Hz, 1H), 7.47-7.32 (m, 6H); $^{13}$C NMR (100.5 MHz, $CDCl_3$): δ 149.4, 146.5, 140.2, 136.8, 135.4, 126.4, 123.8, 121.0, 120.9, 120.6, 109.2.

Dicbz-Bipy (2). A mixture of 1 (1.500 g, 4.641 mmol), bis(pinacolato)diboron (0.648 g, 2.55 mmol), [1,1'-bis(diphenylphosphino)-ferrocene]dichloropalladium(II) (114 mg, 0.139 mmol), potassium acetate (1.367, 13.92 mmol) and DMSO (38 mL) was degassed with argon for 30 min while stirring. The reaction mixture was then maintained at 90° C. with stirring under argon for 46 h. Upon cooling to RT, the reaction was poured over dichloromethane (250 mL) and the organics washed with sat. $NaHCO_3$, water (4×) and brine. The organic phase was then dried over $MgSO_4$, filtered and concentrated in vacuo. Purification of the crude product by flash chromatography ($SiO_2$, 49:1 dichloromethane-acetone) and subsequent recrystallization from hexanes and dichloromethane (ca. 2:1) yielded 2 (1.09 g, 96%) as an off-white solid: mp=239-241° C.; $^1$H NMR (400 MHz, $CDCl_3$): δ 9.01 (dd, J=11.0, 2.2 Hz, 4H), 8.21 (t, J=2.2 Hz, 2H), 8.17 (d, J=7.7 Hz, 4H), 7.45 (d, J=3.3 Hz, 8H), 7.36-7.32 (m, 4H); $^{13}$C NMR (100.5 MHz, $CDCl_3$): δ 148.4, 146.6, 140.4, 135.1, 133.7, 132.6, 126.4, 123.8, 120.9, 120.6, 109.2; Anal. Calcd. for $C_{34}H_{22}N_4$: C, 83.93; H, 4.56; N, 11.51. Found: C, 83.43; H, 4.57; N, 11.32.

The spectroscopic properties of 2 in chloroform were obtained, and the results are depicted in FIG. 1.

EXAMPLE 2

Fabrication of Device C: ITO coated glass substrates were cleaned by ultrasound in acetone and 2-propanol, consecutively, then baked at 110° C. for 3 hours, followed by treatment with oxygen plasma for 5 min. A layer of PEDOT: PSS (Baytron P from H. C. Starck) was spin-coated at 3000 rpm onto the pre-cleaned and O$_2$-plasma treated (ITO)-substrate and annealed at 180° C. for 10 min, yielding a thickness of around 40 nm. In a glove-box hosted vacuum deposition system at a pressure of $10^{-7}$ torr (1 torr=133.322 Pa), 4,4'4"-tri(N-carbazolyl)triphenylamine (TCTA) was first deposited on top of PEDOT/PSS layer at deposition rate of 0.06 nm/s, yielding a 30 nm thick film. Then Dicbz-Bipy and platinum (II)(2-(4',6'-difluorophenyl)pyridinato-N,C$^{2'}$)(2,4-pentanedionato) (FPt) were concurrently heated and deposited on top of TCTA under different deposition speed to make FPt at 12 wt %, followed by deposition of 2,9-dimethyl-4,7-diphenyl-1,10-phenanthroline (BCP) at deposition rate around 0.06 nm/s. CsF and Al were then deposited successively at deposition rates of 0.005 and 0.2 nm/s, respectively. Each individual device has an area of 0.14 cm$^2$. All spectra were measured with an Ocean Optics HR 4000 spectrometer and I-V-L characteristics were taken with a Keithley 2400 SourceMeter and Newport 2832-C power meter and 818 UV detector. All device operation was performed inside a nitrogen-filled glove-box.

EXAMPLE 3

The ambipolar property of Dicbz-Bipy was evaluated using Devices A and B. Device A was fabricated as following: ITO-coated glass substrates were cleaned by ultrasound in acetone and 2-propanol, consecutively, then baked at 110° C. for 3 hours, followed by treatment with oxygen plasma for 5 min. A layer of PEDOT: PSS (Baytron P from H. C. Starck) was spin-coated at 3000 rpm onto the pre-cleaned and O$_2$-plasma treated (ITO)-substrate and annealed at 180° C. for 10 min, yielding a thickness of around 40 nm. In a glove-box hosted vacuum deposition system at a pressure of $10^{-7}$ torr (1 torr=133.322 Pa) was Dicbz-Bipy first deposited on top of PEDOT/PSS layer at deposition rate of 0.06 nm/s, followed by deposition of Al at deposition rates of 0.2 nm/s.

Figure 2:
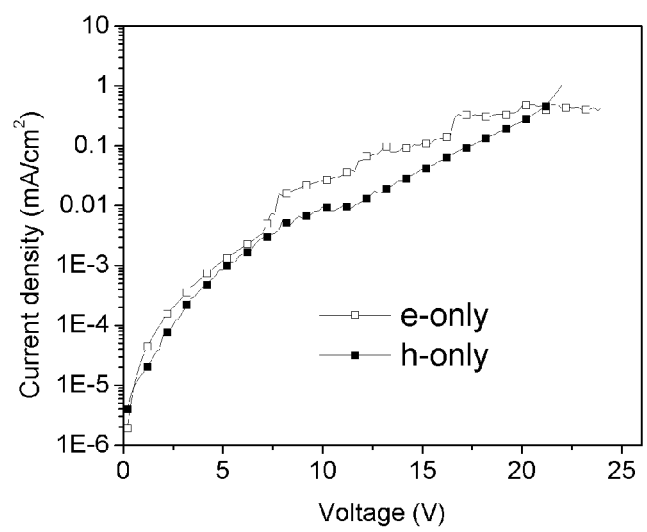
FIG. 2 is a current density vs. voltage plot of two embodiments of the light-emitting devices.

Device B was fabricated as following: ITO-coated glass substrates were cleaned by ultrasound in acetone and 2-propanol, consecutively, then baked at 110° C. for 3 hours, followed by treatment with oxygen plasma for 5 min. In a glove-box hosted vacuum deposition system at a pressure of $10^{-7}$ torr (1 torr=133.322 Pa) was a layer of Al first deposited at deposition rates of 0.2 nm/s, followed by deposition of Dicbz-Bipy at deposition rate of 0.06 nm/s. CsF and Al were then deposited successively at deposition rates of 0.005 and 0.2 nm/s, respectively. The I-V spectra of Device A and Device B are shown in FIG. 2, showing balanced hole-current and electron-current, indicating Dicbz-Bipy has ambipolar property. Note that there is no any detectable electroluminescence (EL) during the measurements in each device, ensuring unipolar injection.

EXAMPLE 4

Figure 3:
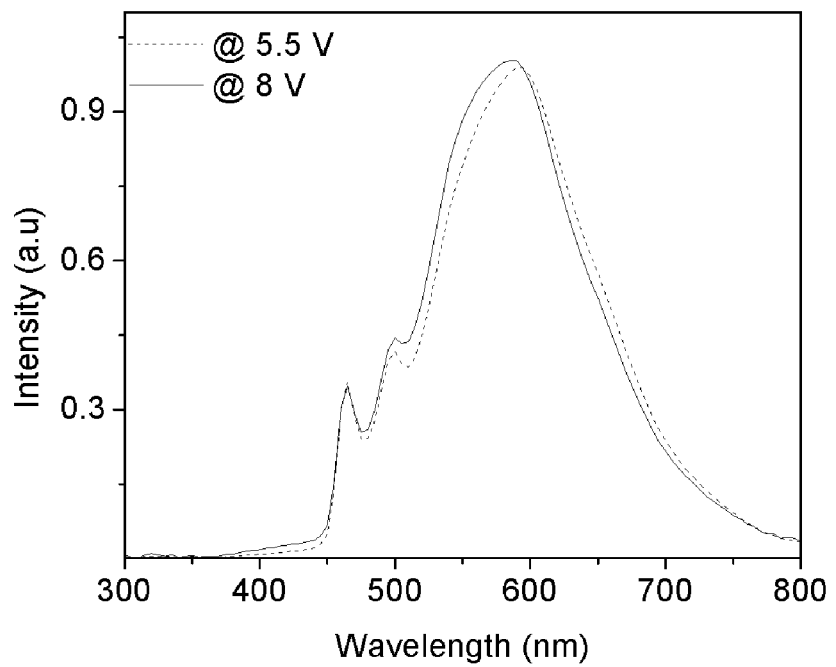
FIG. 3 is the electroluminescence spectrum of one embodiment of the light-emitting device.

Electroluminescence (EL) spectrum of Device C was collected at two different driving voltages, 5.5 V and 8 A (FIG. 3). The CIE and CRI values were also determined at different driving voltages. The CIE color coordinates (X, Y) is defined as the achromatic point. The X and Y color coordinates are weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best. At 5.5 V, the CIE of Device C was (0.45, 0.46) and the CRI value was 73. At 8 V, the CIE was (0.43, 0.46), and the CRI value was 70.

Figure 4:
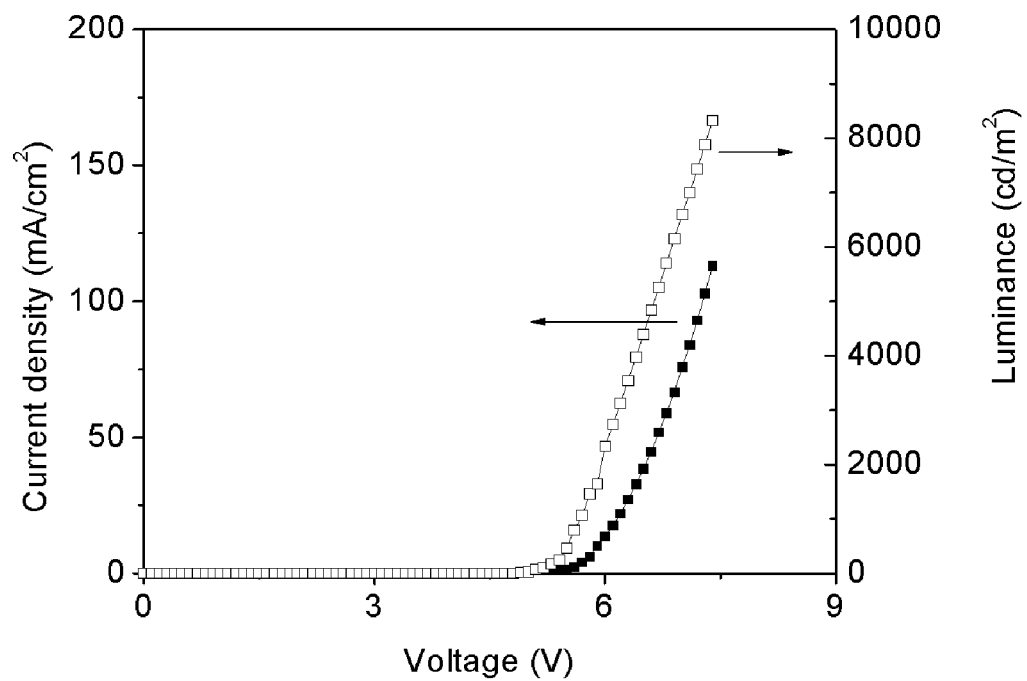
FIG. 4 is a current density vs. voltage curve of the light-emitting devices in FIG. 3.
Figure 5:
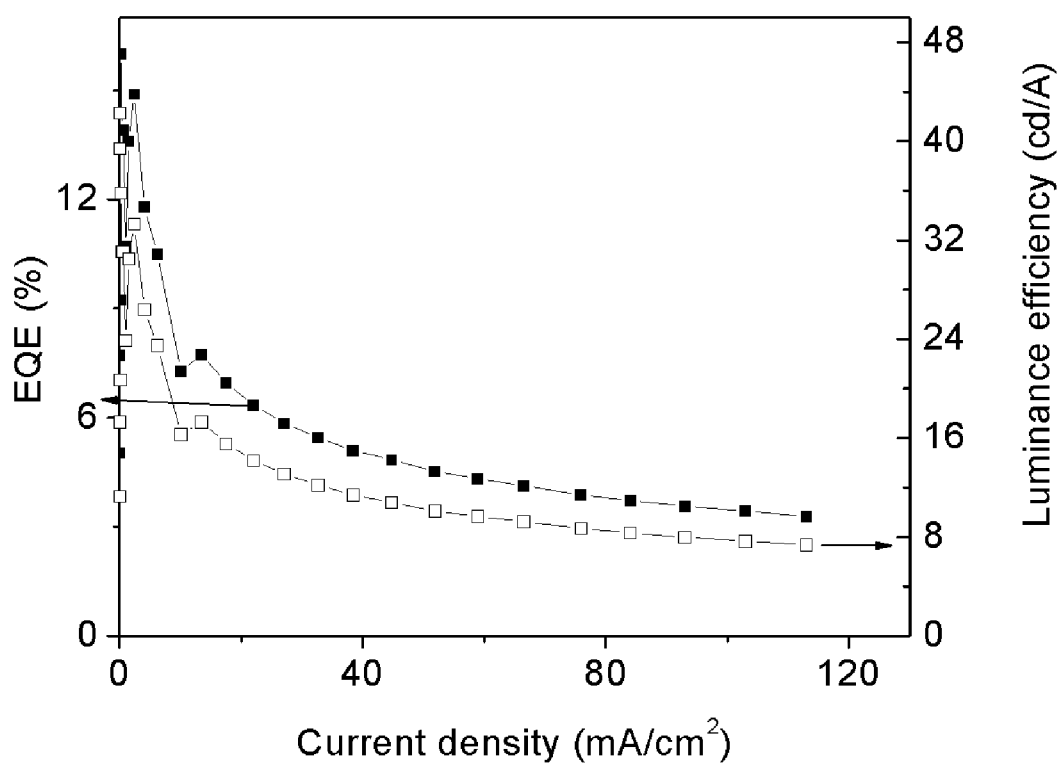
FIG. 5 shows the EQE (external quantum efficiency) and the luminance efficiency with respect to the current density of the light-emitting device featured in FIG. 3.

In addition, device performance of Device C was evaluated by measuring the current density and luminance as a function of the driving voltage, as shown in FIG. 4. The turn-on voltage for Device C was about 4.7 volts and the maximum luminance was about 8000 cd/m$^2$. FIG. 5 shows the EQE (external quantum efficiency) and luminous efficiency as a function of current density. The EQE of Device C was about 11.8%, and the luminous efficiency was about 26.4 cd/A. The power efficiency (PE) was 14.5 lm/w at 1000 cd/m$^2$.

EXAMPLE 5

Example of Measuring Charge Mobility from Space Charge Limited Current (SCLC) Regime The usefulness of the compound disclosed herein is demonstrated by their charge mobility. The carrier mobility of an organic thin film can be derived from the space charge limited current in the current-voltage (IV) measurement based on the Mott's steady state SCLC model $$J = \frac{9\varepsilon\varepsilon_0\mu V^2}{8L^3}$$

where $\epsilon_0$ is the vacuum permittivity, $\epsilon$ is the relative permittivity of the organic layer, $\mu$ is the carrier mobility of the organic layer, V is the voltage bias and L is the thickness of the organic layer.

To evaluate the electron and hole mobility of an organic layer, single-carrier devices (electron-only and hole-only devices) may be made. Electron-only devices may have Al/organic layer/LiF/Al structure with Al as the anode and LiF/Al as the cathode. The LiF/Al electrode has a low work function (~2.6 eV) which can facilitate the injection of electrons into the lower lying LUMO of the organic layer. By contrast, Al has a relatively lower work function (4.28 eV) than the HOMO (5~6 eV) of the organic layer being investigated, which prevents the hole injection from the anode. Thus, only electrons are injected into the organic layer and the electron mobility may be measured as the only charge carrier in the organic layer.

The hole-only devices may have the ITO/PEDOT/organic layer/Al with ITO as the anode and Al as the cathode. The high work function of PEDOT (5.2-5.4 eV) facilitates hole injection from the anode into the organic layer. By contrast, the work function (4.28 eV) of Al is higher than the LUMO of the organic layer (2~4 eV), which preventing the electron injection from the cathode. Thus, only holes are injected into the organic layer, and the hole mobility may be measured as the only charge carrier in the organic layer.

The thickness of the organic layer is kept at 100 nm in both cases.

To measure the space charge limited current, one applies a large voltage scan (0-10 V) on the device to ensure at large current limit the device is under SCLC condition. And then the IV curve is fitted by the SCLC model mentioned above. The carrier mobility can then be derived from the fitting parameters. Electron- and hole-mobility can be derived from the electron-only and hole-only devices for the same organic layer, respectively.

EXAMPLE 6

Fabrication for single-carrier devices: the substrates (ITO coated glass for hole-only devices and glass for electron only devices) were cleaned by detergent, ultrasonic bath in acetone and consecutively in 2-propanol, and baked at 110° C. for 3 hours. For hole-only devices, the precleaned ITO substrates first underwent a UV-ozone treatment for 30 min. A layer of PEDOT: PSS (Baytron P purchased from H. C. Starck) was spin-coated at 6000 rpm onto the substrates and annealed at 180° C. in a glove box for 30 min, yielding a thickness of around 20 nm. In a glove-box hosted vacuum deposition system at a pressure of $10^{-7}$ torr (1 torr=133.322 Pa), a 100 nm-thick layer of the organic compound to be evaluated was first deposited by thermal evaporation on top of PEDOT/PSS layer at deposition rate of 0.1 nm/s. A 50 nm-thick Al layer was then deposited successively by thermal evaporation at deposition rate of 0.3 nm/s, through a shadow mask to define the device area.

For electron-only devices, in a glove-box hosted vacuum deposition system at a pressure of $10^{-7}$ torr (1 torr=133.322 Pa), 20 nm thick Al bottom electrodes were deposited at deposition rate of 0.3 nm/s, through a shadow mask. A 100 nm-thick layer of the organic compound to be evaluated was subsequently deposited onto the substrates at deposition rate of 0.1 nm/s. The top electrode LiF and Al were then deposited successively through a shadow mask, at deposition rates of 0.02 and 0.3 nm/s to achieve the thickness of 1.4 nm and 50 nm, respectively.

The device areas for hole-only and electron-only devices are 0.08 and 0.04 cm², respectively. I-V measurements were carried out using a Keithley 2400 Source Meter to apply 0-10 V voltage scans and measure the current simultaneously. All device operations were done inside a nitrogen-filled glovebox. The high-current end of the IV curves (6-10 V) were fitted by the SCLC model $$J = \frac{9\varepsilon\varepsilon_0\mu V^2}{8L^3}.$$

The electron- and hole-mobility can then be derived from the fitting parameters for the electron-only and hole-only devices, respectively. This method may be adapted to any host compound by replacing the JC-HT3 with the host compound to be tested.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An organic white light-emitting diode device comprising:
 a cathode;
 an anode; and
 an organic component, disposed between the anode and the cathode,
 wherein the organic component comprises a white light-emitting component, and a host compound represented by Formula 1:

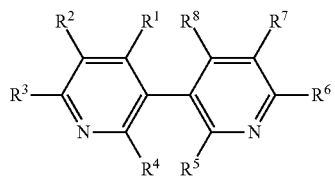

(Formula 1)

wherein $R^1$, $R^2$, $R^3$, $R^6$, $R^7$, and $R^8$ are independently selected from the group consisting of H, optionally substituted $C_{1-12}$ alkyl, optionally substituted phenyl, optionally substituted carbazolyl, optionally substituted diphenylamine, optionally substituted carbazolylphenyl, and optionally substituted diphenylaminophenyl;

provided that: at least one of $R^1$, $R^2$, and $R^3$ is selected from optionally substituted carbazolyl, optionally substituted diphenylamine, optionally substituted carbazolylphenyl, and optionally substituted diphenylaminophenyl, and at least one of $R^6$, $R^7$, and $R^8$ is selected from optionally substituted carbazolyl, optionally substituted diphenylamine, optionally substituted carbazolylphenyl, and optionally substituted diphenylaminophenyl; and $R^4$ and $R^5$ are independently selected from the group consisting of H, optionally substituted $C_{1-12}$ alkyl, optionally substituted phenyl, optionally substituted diphenylamine and optionally substituted diphenylaminophenyl.

2. The device of claim 1, wherein the host compound is the following:

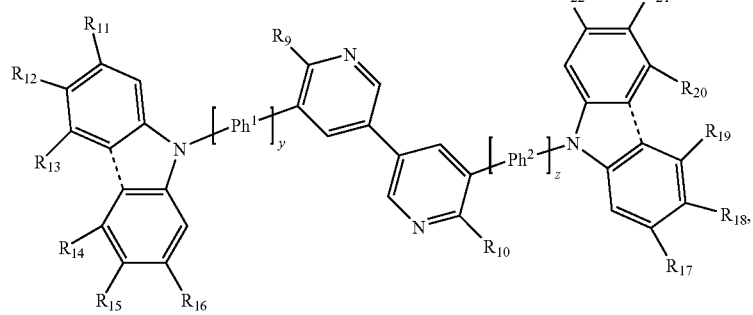

(Formula 2)

wherein each dotted line is independently an optional bond,

Ph¹ and Ph² are independently optionally substituted 1,4-interphenylene or optionally substituted 1,3-interphenylene, y and z are independently 0 or 1;

$R^9$ and $R^{10}$ are independently H, $C_{1-3}$ alkyl, or $C_{1-3}$ perfluoroalkyl; and $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently selected from the group consisting of H, $C_{1-12}$ alkyl, $C_{1-6}F_{1-13}$ fluoroalkyl, and optionally substituted phenyl.

3. The device of claim 1, wherein the host compound is selected from:

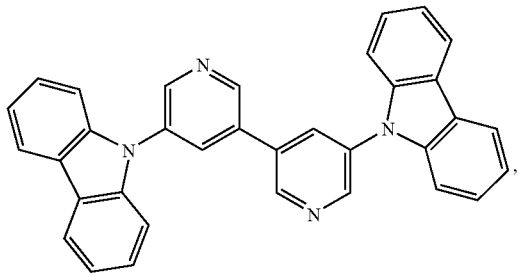

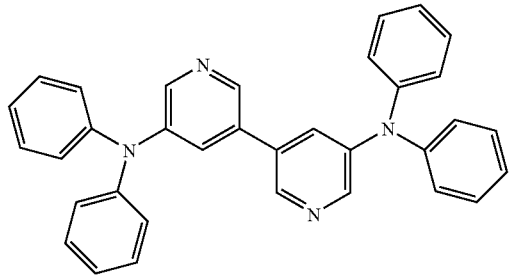

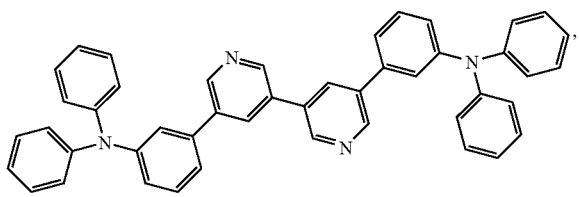

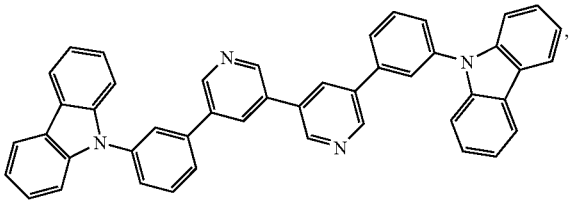

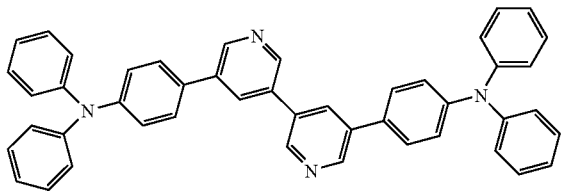

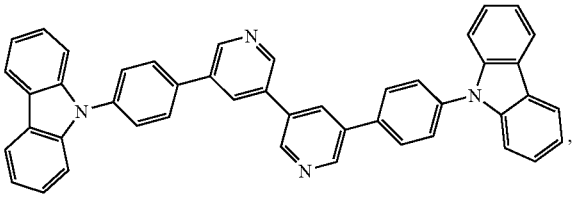

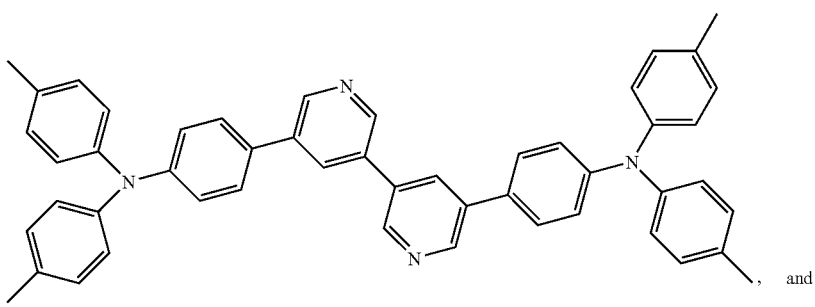

, and

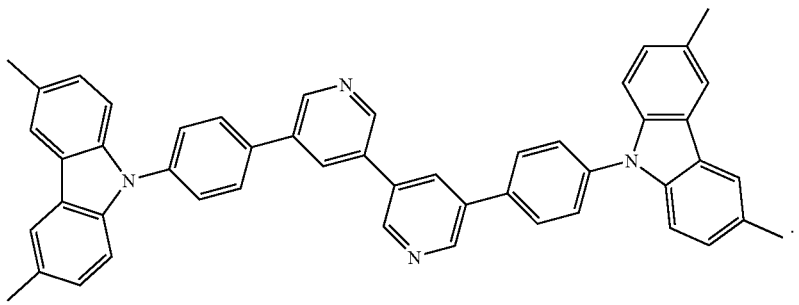

.

4. The device of claim 1, wherein the host compound is:

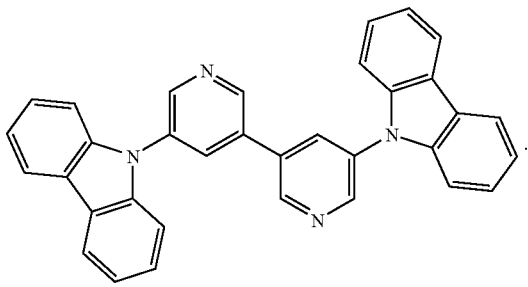

5. The device of claim 1, wherein the white light-emitting component comprises a blue light-emitting component, a green light-emitting component, and a red light-emitting component.

6. The device of claim 5, wherein the blue light-emitting component emits visible photons having an average wavelength in the range of about 440 nm to about 490 nm.

7. The device of claim 5, wherein the green light-emitting component emits visible photons having an average wavelength in the range of about 490 nm to about 600 nm.

8. The device of claim 5, wherein the red light-emitting component emits visible photons having an average wavelength in the range of about 600 nm to about 800 nm.

9. The device of claim 5, wherein the blue light-emitting component comprises a compound selected from the group consisting of: bis-{2-[3,5-bis(trifluoromethyl)phenyl]pyridinato-N,C2'}iridium(III)-picolinate, bis(2-[4,6-difluorophenyl]pyridinato-N,C2')iridium (III) picolinate, bis(2-[4,6-difluorophenyl]pyridinato-N,C2')iridium(acetylacetonate), Iridium (III) bis(4,6-difluorophenylpyridinato)-3-(trifluoromethyl)-5-(pyridine-2-yl)-1,2,4-triazolate, Iridium (III) bis(4,6-difluorophenylpyridinato)-5-(pyridine-2-yl)-1H-tetrazolate, and bis[2-(4,6-difuluorophenyl)pyridinato-N,C$^2$]iridium(III)tetra(1-pyrazolyl)borate.

10. The device of claim 5, wherein the green light-emitting component comprises a compound selected from the group consisting of: Bis(2-phenylpyridinato-N,C2')iridium(III)(acetylacetonate), Bis(2-(4-tolyl)pyridinato-N,C2')iridium (III)(acetylacetonate), Bis(2-(4-tert-butyl)pyridinato-N,C2')iridium (III)(acetylacetonate), Tris(2-phenylpyridinato-N,C2')iridium (III), Bis(2-phenyloxazolinato-N,C2')iridium (III) (acetylacetonate), and Tris(2-(4-tolyl)pyridinato-N,C2')iridium(III).

11. The device of claim 5, wherein the red light-emitting component comprises a compound selected from the group consisting of: Bis[2-(2'-benzothienyl)-pyridinato-N,C3']iridium (III)(acetylacetonate); Bis[(2-phenylquinolyl)-N,C2']iridium (III) (acetylacetonate); Bis[(1-phenylisoquinolinato-N,C2')]iridium (III) (acetylacetonate); Bis[(dibenzo[f,h]quinoxalino-N,C2')iridium (III)(acetylacetonate); Tris(2,5-bis-2'-(9',9'-dihexylfluorene)pyridine)iridium (III); Tris[1-phenylisoquinolinato-N,C2']iridium (III); Tris-[2-(2'-benzothienyl)-pyridinato-N,C3']iridium (III); Tris[1-thiophen-2-ylisoquinolinato-N,C3']iridium (III); and Tris[1-(9,9-dimethyl-9H-fluoren-2-yl)isoquinolinato-(N,C3')iridium (III)).

12. The device of claim 1, wherein the organic component further comprises a white light-emitting layer comprising a blue light-emitting component, a green light-emitting component, and a red light-emitting component.

13. The device of claim 12, wherein the white light-emitting layer further comprises the host compound.

14. The device of claim 13, wherein:
the blue light-emitting component comprises a compound selected from the group consisting of: bis-{2-[3,5-bis(trifluoromethyl)phenyl]pyridinato-N,C2'}iridium(III)-picolinate, bis(2-[4,6-difluorophenyl]pyridinato-N,C2')iridium (III) picolinate, bis(2-[4,6-difluorophenyl]pyridinato-N,C2')iridium(acetylacetonate), Iridium (III) bis(4,6-difluorophenylpyridinato)-3-(trifluoromethyl)-5-(pyridine-2-yl)-1,2,4-triazolate, Iridium (III) bis(4,6-difluorophenylpyridinato)-5-(pyridine-2-yl)-1H-tetrazolate, and bis[2-(4,6-difuluorophenyl)pyridinato-N,C$^{2'}$]iridium(III)tetra(1-pyrazolyl)borate;
the green light-emitting component comprises a compound selected from the group consisting of: Bis(2-phenylpyridinato-N,C2')iridium(III)(acetylacetonate), Bis(2-(4-tolyl)pyridinato-N,C2')iridium(III)(acetylacetonate), Bis(2-(4-tert-butyl)pyridinato-N,C2')iridium (III)(acetylacetonate), Tris(2-phenylpyridinato-N,C2') iridium (III), Bis(2-phenyloxazolinato-N,C2')iridium (III) (acetylacetonate), and Tris(2-(4-tolyl)pyridinato-N,C2')iridium(III); and
the red light-emitting component comprises a compound selected from the group consisting of: Bis[2-(2'-benzothienyl)-pyridinato-N,C3']iridium (III)(acetylacetonate); Bis[(2-phenylquinolyl)-N,C2']iridium (III) (acetylacetonate); Bis[(1-phenylisoquinolinato-N,C2')] iridium (III) (acetylacetonate); Bis[(dibenzo[f,h]quinoxalino-N,C2')iridium (III)(acetylacetonate); Tris(2,5-bis-2'-(9',9'-dihexylfluorene)pyridine)iridium (III); Tris [1-phenylisoquinolinato-N,C2']iridium (III); Tris-[2-(2'-benzothienyl)-pyridinato-N,C3']iridium (III); Tris [1-thiophen-2-ylisoquinolinato-N,C3']iridium (III); and Tris[1-(9,9-dimethyl-9H-fluoren-2-yl)isoquinolinato-(N,C3')iridium (III)).

15. The device of claim 12, wherein the organic component further comprises:
a hole-transport layer disposed between the anode and the white light-emitting layer; and
an electron-transport layer disposed between the cathode and the white light-emitting layer;
wherein at least one of the white light-emitting layer, the hole-transport layer, and the electron-transport layer comprises the host compound.

16. The device of claim 15, wherein all of the white light-emitting layer, the hole-transport layer and the electron-transport layer comprise the host compound.

17. The device of claim 1, wherein the white light-emitting component comprises a blue light-emitting component, and an orange light-emitting component.

18. The device of claim 1, wherein the white light-emitting component comprises an electroluminescent compound which emits white light.

19. The device of claim 1, wherein the white light-emitting component comprises at least one compound selected from the group consisting of:

43 44
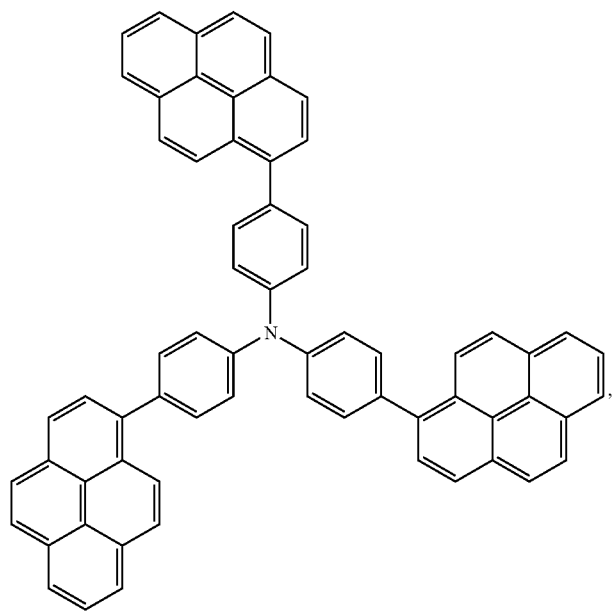
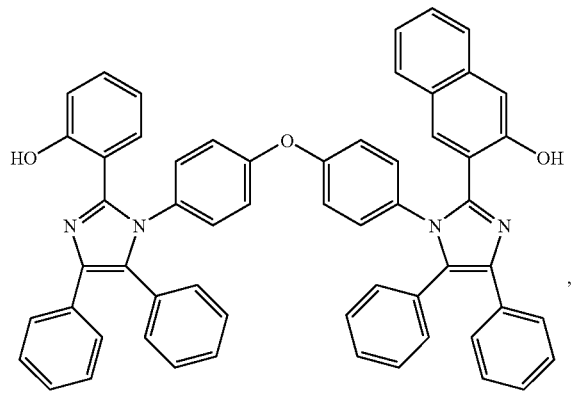
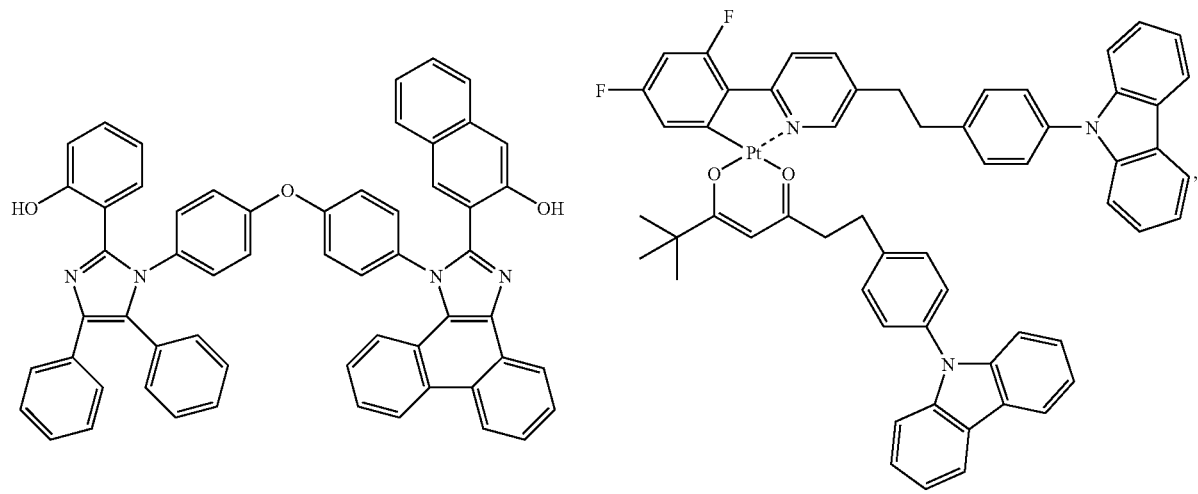
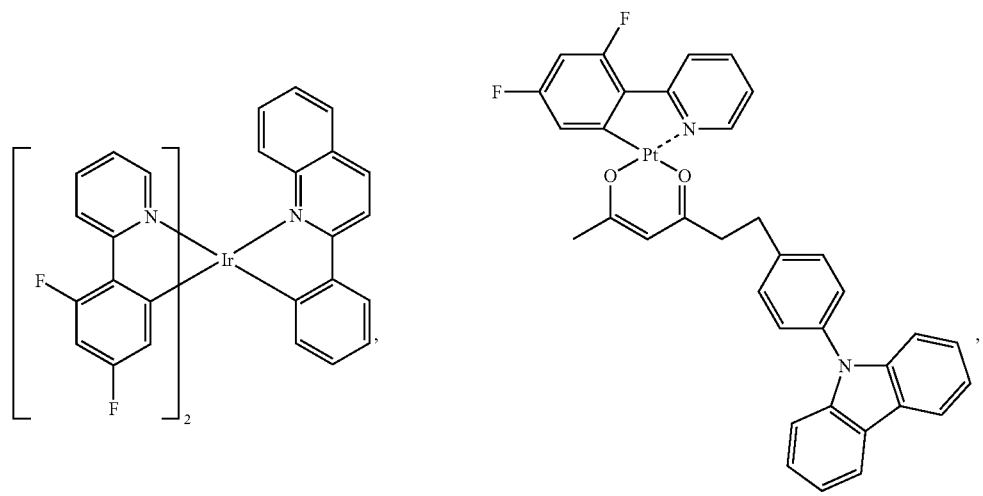

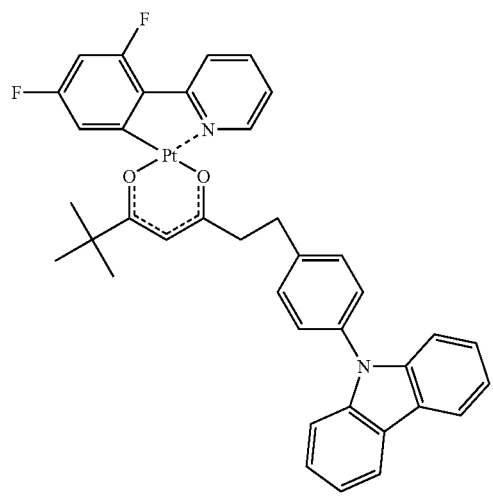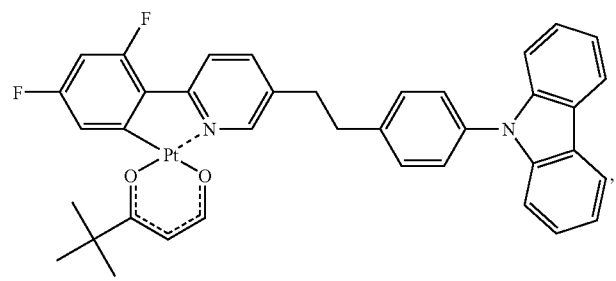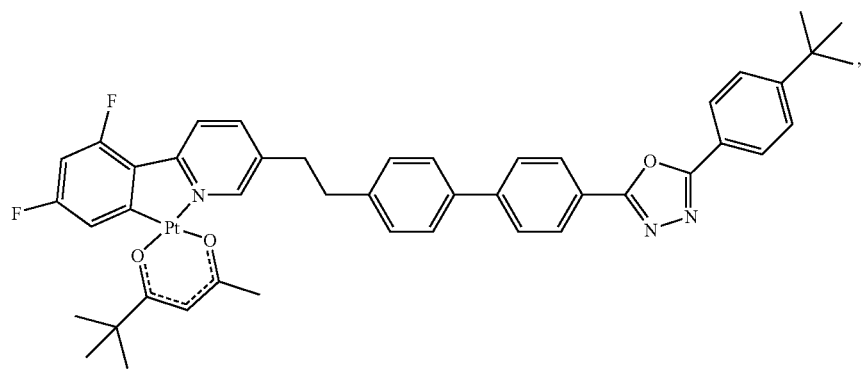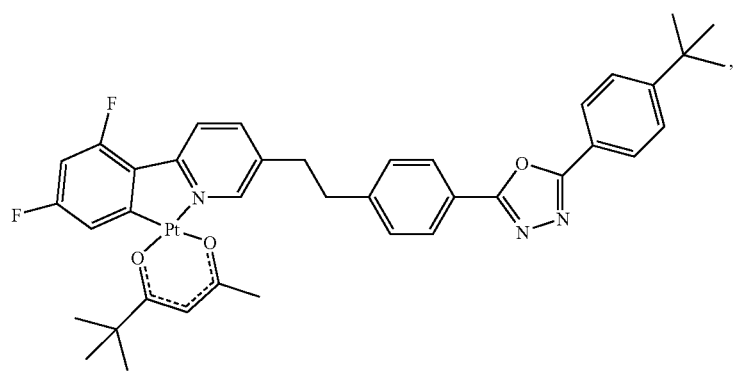

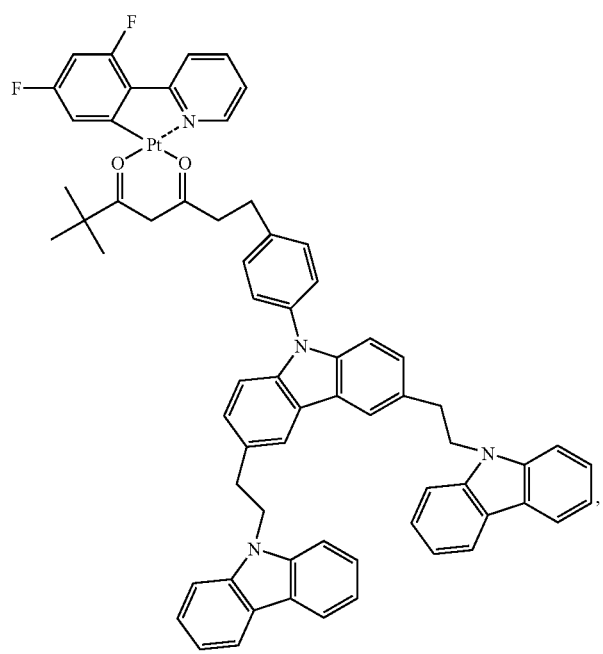
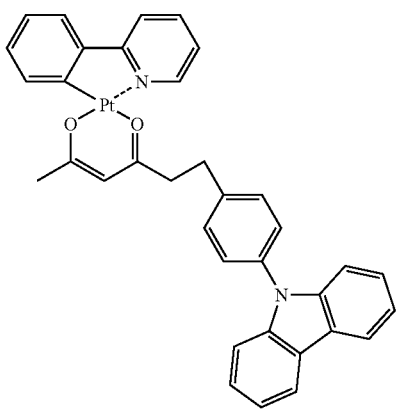
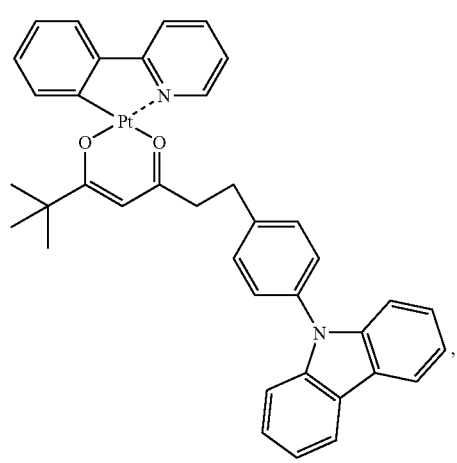
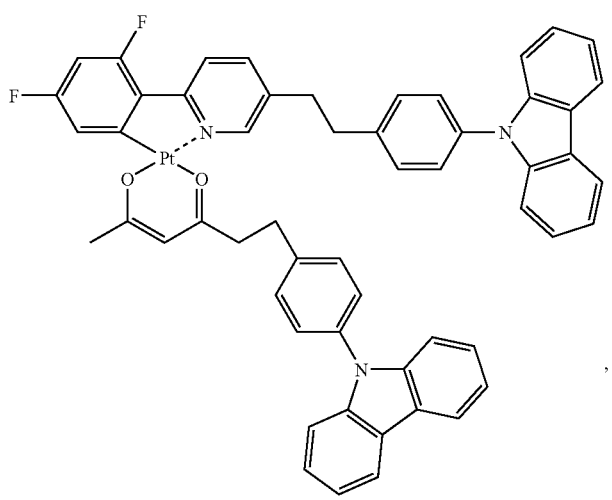
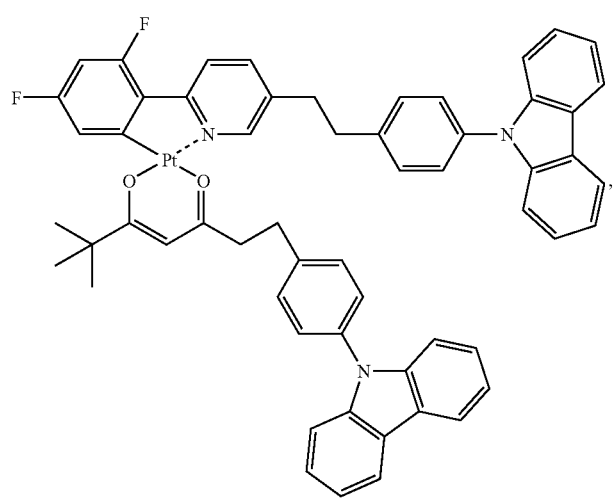
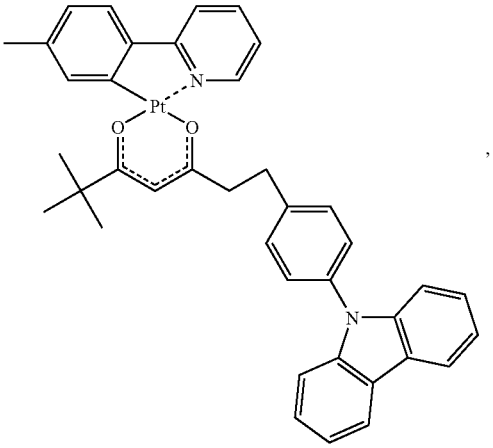

-continued

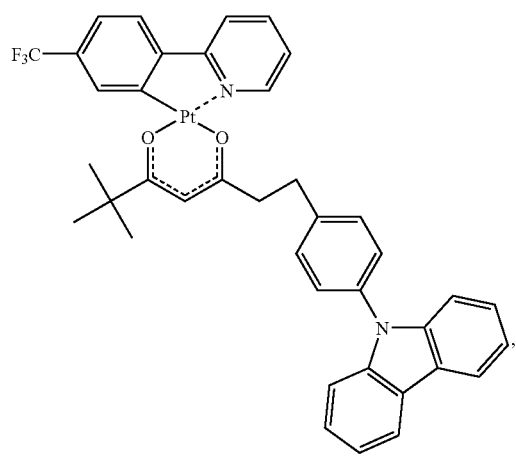

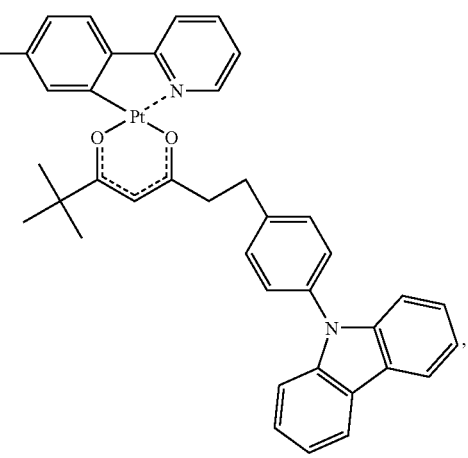

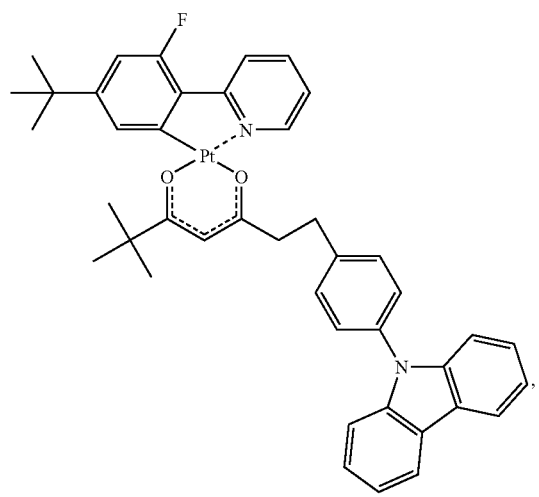

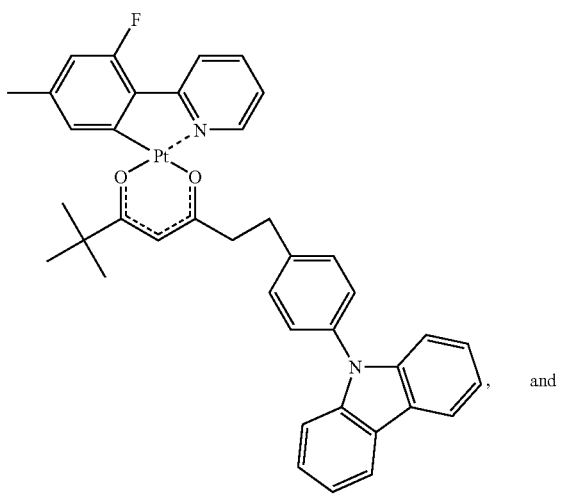

and

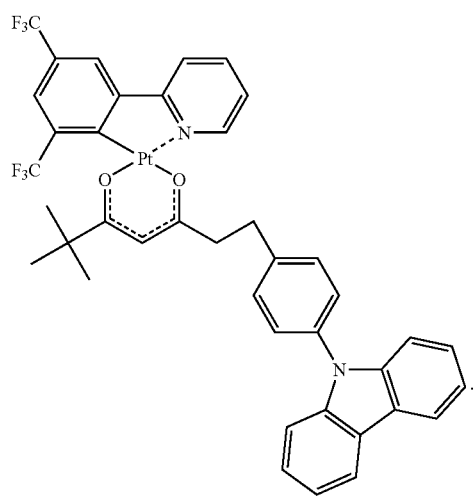

20. An organic light-emitting diode device comprising:
a cathode;
an anode; and
an organic component, disposed between the anode and the cathode,
wherein the organic component comprises a white light-emitting component and a host compound selected from optionally substituted 5,5'-bis(diphenylamino)-3,3'-bipyridine, optionally substituted 6,6'-(dicarbazole-9-yl)-3,3'-bipyridine, optionally substituted 6,6'-bis(diphenylamino)-3,3'-bipyridine, optionally substituted 5,5'-(dicarbazole-9-yl)-3,3'-bipyridine, optionally substituted 5,5'-bis(4-diphenylaminophenyl)-3,3'-bipyridine, optionally substituted 5,5'-bis(4-(3,6-dimethylcarbazol-9-yl)phenyl)-3,3'-bipyridine, optionally substituted 5,5'-bis(4-(carbazol-9-yl)phenyl)-3,3'-bipyridine, optionally substituted 5,5'-bis(4-di(4-methylphenyl)aminophenyl)-3,3'-bipyridine, optionally substituted 4,4'-(3,3'-bipyridine-6,6'-diyl)bis(N,N-diphenylaniline), optionally substituted 5,5'-bis(3-diphenylaminophenyl)-3,3'-bipyridine, optionally substituted 5,5'-bis(3-(carbazol-9-yl)phenyl)-3,3'-bipyridine, and optionally substituted 6,6'-bis(4-(carbazol-9-yl)phenyl)-3,3'-bipyridine.

* * * * *